US012649002B2

(12) United States Patent
Pietri-Rouxel et al.

(10) Patent No.: US 12,649,002 B2
(45) Date of Patent: **\*Jun. 9, 2026**

(54) COMBINED THERAPY FOR MUSCULAR DISEASES

(71) Applicants:ASSOCIATION INSTITUT DE MYOLOGIE, Paris (FR); INSERM (INSTITUT NATIONAL DE LA SANTÉ ET DE LA RECHERCHE MÉDICALE), Paris (FR); SORBONNE UNIVERSITE, Paris (FR)

(72) Inventors: France Pietri-Rouxel, Clichy la Garenne (FR); Sestina Falcone, Paris (FR)

(73) Assignees: ASSOCIATION INSTITUT DE MYOLOGIE, Paris (FR); INSERM (INSTITUT NATIONAL DE LA SANTÉ ET DE LA RECHERCHE MÉDICALE), Paris (FR); SORBONNE UNIVERSITE, Paris (FR)

( * ) Notice: Subject to any disclaimer, the term of this patent is extended or adjusted under 35 U.S.C. 154(b) by 987 days.

This patent is subject to a terminal disclaimer.

(21) Appl. No.: 17/774,732

(22) PCT Filed: Nov. 5, 2020

(86) PCT No.: PCT/EP2020/081200
§ 371 (c)(1),
(2) Date: May 5, 2022

(87) PCT Pub. No.: WO2021/089736
PCT Pub. Date: May 14, 2021

(65) Prior Publication Data
US 2022/0387624 A1 Dec. 8, 2022

(30) Foreign Application Priority Data
Nov. 6, 2019 (EP) .................................... 19207561

(51) Int. Cl.
*A61P 21/00* (2006.01)
*A61K 31/713* (2006.01)
*A61K 48/00* (2006.01)

(52) U.S. Cl.
CPC .......... *A61K 48/005* (2013.01); *A61K 31/713* (2013.01); *A61P 21/00* (2018.01)

(58) Field of Classification Search
CPC .............................. A61K 48/005; A61P 21/00
See application file for complete search history.

(56) References Cited

U.S. PATENT DOCUMENTS

| | | | | |
|---|---|---|---|---|
| 2012/0003191 A1* | 1/2012 | Burkin et al. | ......... | A61K 31/19 424/93.7 |
| 2012/0093801 A1* | 4/2012 | Awad et al. | ........... | A61K 38/17 424/130.1 |
| 2018/0362980 A1* | 12/2018 | Pietri-Rouxel et al. | ..................... | C12N 15/113 |

FOREIGN PATENT DOCUMENTS

| | | | | |
|---|---|---|---|---|
| WO | 2016/198676 | 12/2016 | | |
| WO | WO2017098187 A1 * | 6/2017 | ........... | C12N 15/113 |
| WO | 2020/016425 | 1/2020 | | |

OTHER PUBLICATIONS

Appel et al. (2009) "Synergistic effects of growth and differentiation factor-5 (GDF-5) and insulin on expanded chondrocytes in a 3-D environment" Osteoarthritis and cartilage, 17(11), 1503-1512. (Year: 2009).*
Sun et al. (2021) "Growth differentiation factor 5 in cartilage and osteoarthritis: a possible therapeutic candidate" Cell Proliferation, 54(3), e12998, 13 pages. (Year: 2021).*
Charbord et al. (2013) "High throughput screening for inhibitors of REST in neural derivatives of human embryonic stem cells reveals a chemical compound that promotes expression of neuronal genes" Stem Cells, 31(9), 1816-1828. (Year: 2013).*
Shieh, P. B. (2018) "Emerging strategies in the treatment of Duchenne muscular dystrophy" Neurotherapeutics, 15(4), 840-848. (Year: 2018).*
Pietri-Rouxel et al. "Team 8-Gene Therapy for DMD & Skeletal Muscle Pathophysiology Group", Institut de Myologie, webpage, archived: May 18, 2019, accessed: Aug. 17, 2025 web.archive.org/web/20190518080554/http://www.institut-myologie.org:80/en/recherche-2/centre-de-recherche-en-myologie/team-5-rna-repair-based-therapeutics-skeletal-muscle-pathophysiology. (Year: 2019).*
Falcone et al. "rGdf5, an unexpected treatment against age-related muscle mass loss", In 24th International Annual Congress of the World Muscle Society, Oct. 2019, presentation, 25 slides. (Year: 2019).*
Bethanie I. Ayerst, et al., "Growth Differentiation Factor 5-Mediated Enhancement of Chondrocyte Phenotype Is Inhibited by Heparin: Implications for the Use of Heparin in the Clinic and in Tissue Engineering Applications", Tissue Engineering Part A, vol. 23, No. 7-8, Apr. 1, 2017, pp. 275-292 (18 pages).
Gonzalo Cordova, et al., "Combined Therapies for Duchenne Muscular Dystrophy to Optimize Treatment Efficacy", Frontiers in Genetics, vol. 9, Article 114, Apr. 10, 2018, 8 pages.
Keisuke Hitachi, et al., "Long Non-Coding RNA Myoparr Regulates GDF5 Expression in Denervated Mouse Skeletal Muscle", Non-Coding RNA, vol. 5, No. 2, Apr. 8, 2019, 13 pages.
Cécile Peccate, et al., "Antisense pre-treatment increases gene therapy efficacy in dystrophic muscles", Human Molecular Genetics, vol. 25, No. 16, Aug. 15, 2016, pp. 3555-3563 (9 pages).
France Pietri-Rouxel, "Team 8-Gene Therapy for DMD & Skeletal Muscle Pathophysiology Group—Institut de Myologie", Aug. 30, 2019, 2 pages, http://web.archive.org/web/20190830183725/https://www.institute-myologie.org/en/recherche-2/centre-de-recherche-en-myologie/team-5-rna-repair-based-therapeutics-skeletal-muscle-pathophysiology/.

(Continued)

*Primary Examiner* — James Joseph Graber
(74) *Attorney, Agent, or Firm* — INIXON & VANDERHYE, PC

(57) ABSTRACT
The present invention relates to the treatment of muscular diseases.

Figure 1:
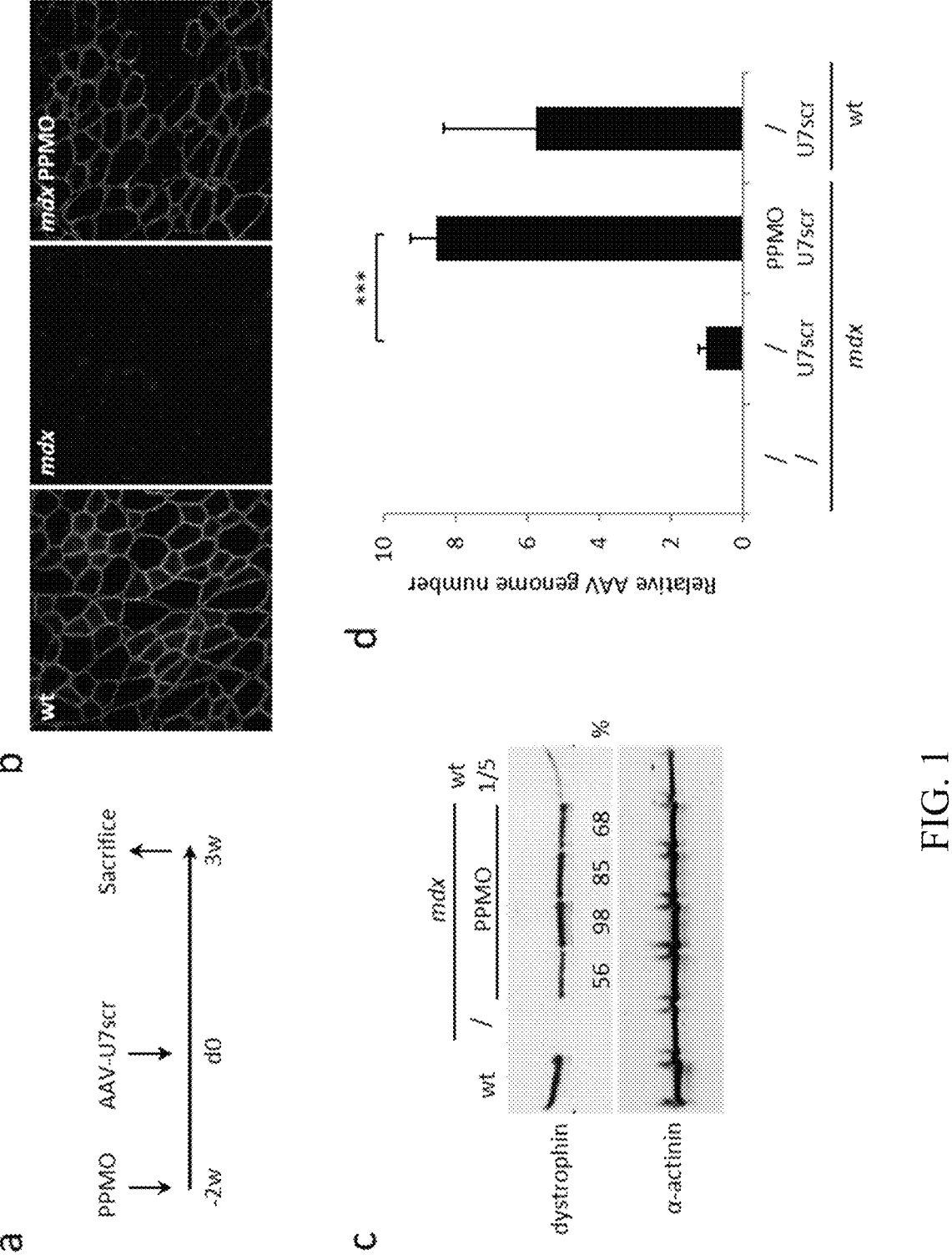

6 Claims, 7 Drawing Sheets
Specification includes a Sequence Listing.

(56)　　　　　　References Cited

OTHER PUBLICATIONS

M. Traore, et al., "P.133A novel CaVβ1 isoform connecting voltage sensing with muscle mass homeostasis", Neuromuscular Disorders, Elsevier Ltd, GB, vol. 29, Sep. 29, 2019, 1 page.

Massiré Traoré, et al., "An embryonic CaVb1 isoform promotes muscle mass maintenance via GDF5 signaling in adult mouse", Science Translational Medicine, vol. 11, No. 517, Nov. 6, 2019, 14 pages.

International Search Report and Written Opinion of the ISA for PCT/EP2020/081200 dated Mar. 4, 2021, 32 pages.

* cited by examiner

SEQUENCE LISTING

<160> NUMBER OF SEQ ID NOS: 19

<210> SEQ ID NO 1
<211> LENGTH: 40
<212> TYPE: DNA
<213> ORGANISM: artificial
<220> FEATURE:
<223> OTHER INFORMATION: antisense oligonucleotide

<400> SEQUENCE: 1
cattcaactg ttgcctccgg ttctgaaggt gttcttgtac                                    40

<210> SEQ ID NO 2
<211> LENGTH: 40
<212> TYPE: DNA
<213> ORGANISM: artificial
<220> FEATURE:
<223> OTHER INFORMATION: antisense oligonucleotide

<400> SEQUENCE: 2
cattcaactg ttgcctccgg ttctgaaggt gttcttgtac                                    40

<210> SEQ ID NO 3
<211> LENGTH: 22
<212> TYPE: DNA
<213> ORGANISM: artificial
<220> FEATURE:
<223> OTHER INFORMATION: primer

<400> SEQUENCE: 3
ctccatcact aggggttcct tg                                                       22

<210> SEQ ID NO 4
<211> LENGTH: 18
<212> TYPE: DNA
<213> ORGANISM: artificial
<220> FEATURE:
<223> OTHER INFORMATION: primer

<400> SEQUENCE: 4
gtagataagt agcatggc                                                            18

<210> SEQ ID NO 5
<211> LENGTH: 17
<212> TYPE: DNA
<213> ORGANISM: artificial
<220> FEATURE:
<223> OTHER INFORMATION: probe

<400> SEQUENCE: 5
tagttaatga ttaaccc                                                             17

<210> SEQ ID NO 6
<211> LENGTH: 3765
<212> TYPE: DNA
<213> ORGANISM: artificial
<220> FEATURE:
<223> OTHER INFORMATION: optimized delta-AB/R3-R18/delta CT

<400> SEQUENCE: 6
gccaccatgc tgtggtggga ggaagtggag gactgctacg agagagagga cgtgcagaag             60
aaaaccttca ccaagtgggt gaacgcccag ttcagcaagc acctggaggc ccctgaggac            120
aagagcttcg gcagcagcct gatggagagc gaagtgaacc tggacagata ccagaccgcc           180
ctggaggaag tgctgagctg gctgctgagc gccgaggaca ccctgcaggc ccagggcgag           240

```
atcagcaacg acgtggaagt ggtgaaggac cagttccaca cccacgaggg ctacatgatg      300
gatctgaccg cccaccaggg cagagtgggc aatatcctgc agctgggcag caagctgatc      360
ggcaccggca agctgagcga ggacgaggag accgaagtgc aggagcagat gaacctgctg      420
aacagcagat gggagtgcct gagagtggcc agcatggaga agcagagcaa cctgcacaga      480
gtgctgatgg acctgcagaa ccagaagctg aaggagctga cgactggct gaccaagacc       540 gaggagcgga ccagaaagat ggaggaggag cccctgggcc ccgacctgga ggacctgaag      600
agacaggtgc agcagcacaa ggagaccgag atcgccgtgc aggccaagca gcccgacgtg      660
gaggagatcc tgagcaaggg ccagcacctg tacaaggaga agcctgccac ccagcccgtg      720
aagagaaagc tggaggatct gagcagcgag tggaaggccg tgaacagact gctgcaggag      780
ctgagagcca aacagcctga cctggcccct ggcctgacca ccatcggcgc cagccccacc      840
cagacagtga ccctggtgac ccagcctgtg gtgaccaagg agacagccat cagcaagctg      900
gagatgccca gctccctgat gctggaagtg cccgccctgg ccgatttcaa tagggcctgg      960
accgagctga ccgattggct gtccctgctg gaccaggtga tcaagagcca gagagtgatg     1020
gtgggcgatc tggaggacat caacgagatg atcatcaagc agaaagccac catgcaggac     1080
ctggagcaga ggagacccca gctggaagag ctgatcacag ccgcccagaa cctgaagaac     1140
aagaccagca accaggaggc caggaccatc atcaccgacc ggatcgagag gatccagaac     1200
cagtgggatg aagtgcagga acacctgcag aacagacggc agcagctgaa cgagatgctg     1260
aaggacagca cccagtggct ggaggccaag gaggaggccg agcaggtgct gggccaggcc     1320
agagccaagc tggagtcctg gaaggagggc ccttacaccg tggatgccat ccagaagaag     1380
atcaccgaga ccaagcagct ggccaaggac ctgagacagt ggcagaccaa cgtggacgtg     1440
gccaatgatc tggccctgaa gctgctgaga gactacagcg ccgacgatac ccggaaagtg     1500
cacatgatca cagagaacat caatgcttct tggcggagca tccacaagag agtgagcgag     1560
agagaagccg ccctggaaga gactcatagg ctgctccagc agttccctct ggacctggag     1620
aagttcctgg cctggctgac agaggccgag accaccgcca cgtgctgca ggacgccacc      1680 agaaaggaga gactgctgga ggatagcaag ggcgtgaagg aactgatgaa gcagtggcag     1740
gatctgcagg gcgaaatcga ggcccacacc gacgtgtacc acaacctgga cgagaacagc     1800
cagaagatcc tgagaagcct ggagggcagc gacgacgccg tgctgctgca gagaaggctg     1860
gacaacatga acttcaagtg gagcgagctg cggaagaaga gcctgaacat ccggagccac     1920
ctggaagcca gcagcgacca gtggaagaga ctgcacctga gcctgcagga actgctggtg     1980
tggctgcagc tgaaggacga cgagctgagc agacaggccc ccatcggcgg cgacttcccc     2040
gccgtgcaga agcagaacga cgtgcaccgg gccttcaaga gggagctgaa aaccaaggaa     2100
cccgtgatca tgagcaccct ggagacagtg cggatcttcc tgaccgagca gcccctggag     2160
ggcctggaga agctgtacca ggagcccaga gagctgcccc cgaggagag agcccagaac      2220 gtgacccggc tgctgagaaa gcaggccgag gaagtgaata ccgagtggga gaagctgaat     2280
ctgcactccg ccgactggca gagaaagatc gacgagaccc tggaacgcct gcaggagctg     2340
caggaagcca ccgacgagct ggacctgaaa ctgaggcagg ccgaagtgat caagggcagc     2400
tggcagcctg tgggcgacct gctgatcgat ccctgcagg accacctgga aaaagtgaag       2460
gccctcaggg gcgagatcgc tcctctgaag gagaatgtga gccacgtgaa cgacctggcc     2520
agacagctga ccaccctggg catccagctg agcccctaca acctgagcac actggaagat     2580
```

-continued

```
ctgaacaccc ggtggaagct gctgcaggtg gccgtggagg atagagtgag gcagctgcac    2640
gaagcccaca gagacttcgg ccctgccagc cagcacttcc tgagcaccag cgtgcagggc    2700
ccctgggaga gagccatctc ccccaacaaa gtgccctact acatcaacca cgagacccag    2760
accacctgct gggaccaccc taagatgacc gagctgtatc agagcctggc cgacctgaac    2820
aatgtgcggt tcagcgccta cagaaccgcc atgaagctgc ggagactgca gaaggccctg    2880
tgcctggacc tgctgagcct gagcgccgcc tgcgacgccc tggaccagca caacctgaag    2940
cagaatgacc agcccatgga catcctgcag atcatcaact gcctgaccac aatctacgat    3000
cggctggagc aggagcacaa caacctggtg aacgtgcccc tgtgcgtgga catgtgcctg    3060
aattggctgc tgaacgtgta cgacaccggc aggaccggca gaatcagagt gctgtccttc    3120
aagaccggca tcatcagcct gtgcaaggcc cacctggagg ataagtaccg ctacctgttc    3180
aagcaggtgg ccagcagcac cggcttctgc gatcagagga gactgggcct gctgctgcac    3240
gatagcatcc agatccctag gcagctgggc gaagtggcca gctttggcgg cagcaacatc    3300
gagccctctg tgaggagctg cttccagttc gccaacaaca gcccgagat cgaggccgcc    3360 ctgttcctgg attggatgag gctggagccc cagagcatgg tgtggctgcc tgtgctgcac    3420
agagtggccg ccgccgagac cgccaagcac caggccaagt gcaacatctg caaggagtgc    3480
cccatcatcg gcttccggta caggagcctg aagcacttca actacgacat ctgccagagc    3540
tgctttttca gcggcagagt ggccaagggc cacaagatgc actaccccat ggtggagtac    3600 tgcacccca ccacctccgg cgaggatgtg agagacttcg ccaaagtgct gaagaataag    3660
ttccggacca agcggtactt tgccaagcac cccaggatgg gctacctgcc cgtgcagacc    3720
gtgctggagg gcgacaacat ggagaccgac accatgtgat gatga    3765
```

```
<210> SEQ ID NO 7
<211> LENGTH: 3606
<212> TYPE: DNA
<213> ORGANISM: artificial
<220> FEATURE:
<223> OTHER INFORMATION: optimized delta R4-R23/delta CT

<400> SEQUENCE: 7
```

```
gccaccatgc tgtggtggga ggaagtggag gactgctacg agagagagga cgtgcagaag     60
aaaaccttca ccaagtgggt gaacgcccag ttcagcaagt tcggcaagca gcacatcgag    120
aacctgttca gcgacctgca ggatggcagg agactgctgg atctgctgga gggactgacc    180
ggccagaagc tgcccaagga gaagggcagc accagagtgc acgccctgaa caacgtgaac    240
aaggccctga gagtgctgca gaacaacaac gtggacctgg tgaatatcgg cagcaccgac    300
atcgtggacg gcaaccacaa gctgaccctg ggcctgatct ggaacatcat cctgcactgg    360
caggtgaaga acgtgatgaa gaacatcatg gccggcctgc agcagaccaa cagcgagaag    420
atcctgctga gctgggtgag gcagagcacc agaaactacc cccaggtgaa cgtgatcaac    480
ttcaccacct cctggagcga cggcctggcc ctgaacgccc tgatccacag ccacagaccc    540
gacctgttcg actggaacag cgtggtgtgt cagcagagcg ccacccagag actggagcac    600
gccttcaaca tcgccagata ccagctgggc atcgagaagc tgctggaccc cgaggacgtg    660
gacaccacct accccgacaa gaaaagcatc ctgatgtata ttacctctct gtttcaggtg    720 ctgcccagc aggtgtccat cgaggccatc caggaagtgg aaatgctgcc caggcccccc    780
aaagtgacca aggaggagca cttccagctg caccaccaga tgcactatag ccagcagatc    840
accgtgtccc tggcccaggg ctatgagaga accagcagcc ccaagcccag attcaagagc    900
```

-continued

```
tacgcctaca cccaggccgc ctacgtgacc acctccgacc ccaccagaag ccccttcccc     960
agccagcacc tggaggcccc cgaggacaag agcttcggca gcagcctgat ggagagcgaa    1020
gtgaacctgg acagatacca gaccgccctg gaggaagtgc tgtcttggct gctgtccgcc    1080
gaggacaccc tgcaggccca gggcgagatc agcaacgacg tggaagtggt gaaggaccag    1140
ttccacaccc acgagggcta catgatggat ctgaccgccc accagggcag agtgggcaat    1200
atcctgcagc tgggcagcaa gctgatcggc accggcaagc tgagcgagga cgaggagacc    1260
gaagtgcagg agcagatgaa cctgctgaac agcagatggg agtgcctgag agtggccagc    1320
atggagaagc agagcaacct gcaccgcgtg ctgatggacc tgcagaacca gaagctgaag    1380
gagctgaacg actggctgac caagaccgag gagcggacca gaaagatgga ggaggagccc    1440
ctgggccccg acctggagga cctgaagaga caggtgcagc agcacaaagt gctgcaggag    1500
gacctggaac aggagcaggt gcgcgtgaac agcctgaccc acatggtggt cgtggtggac    1560
gagagcagcg gcgaccacgc cacagccgcc ctggaagagc agctgaaagt gctgggcgac    1620
agatgggcca acatctgccg gtggaccgag gacagatggg tgctgctgca ggacatcctg    1680
ctgaagtggc agagactgac agaggagcag tgcctgttta gcgcctggct gagcgagaag    1740
gaggacgccg tgaacaagat ccacaccacc ggcttcaagg accagaacga gatgctgagc    1800
agcctgcaga gctggccgt gctgaaggcc gatctggaga agaaaaagca gagcatgggc    1860
aagctgtact ccctgaagca ggacctgctg tccaccctga agaacaagag cgtgacccag    1920
aaaaccgagg cctggctgga caatttcgcc cggtgctggg acaatctggt gcagaaactg    1980
gagaagagca ccgcccagat cagccaggcc gtgaccacca cccagcccag cctgacacag    2040
accaccgtga tggagaccgt gaccacagtg accaccaggg agcagatcct ggtgaagcac    2100
gcccaggagg agctgcccc tccccccct cagaagaagc ggcagatcac agtggacacc    2160
ctggagagac tgcaggagct gcaggaagcc accgacgagc tggacctgaa gctgagacag    2220
gccgaagtga tcaagggcag ctggcagcct gtgggcgatc tgctgatcga cagcctgcag    2280
gaccacctgg agaaagtgaa ggccctgcgg ggcgagatcg cccccctgaa ggagaatgtg    2340
agccacgtga acgacctggc cagacagctg accaccctgg gcatccagct gagcccctac    2400
aatctgagca ccctggaaga tctgaacacc cggtggaaac tgctgcaggt ggccgtggag    2460
gatagagtga ggcagctgca cgaggccac agagacttcg ccctgcctc ccagcacttc    2520 ctgagcacca gcgtgcaggg cccctgggag agagccatct cccccaacaa agtgccctac    2580
tacatcaacc acgagaccca gaccacctgc tgggaccacc ctaagatgac cgagctgtac    2640
cagagcctgg ccgacctgaa caatgtgcgg ttcagcgcct acagaaccgc catgaagctg    2700
cggagactgc agaaggccct gtgcctggac ctgctgagcc tgagcgccgc ctgcgacgcc    2760
ctggaccagc acaacctgaa gcagaacgac cagcccatgg acattctgca gatcatcaac    2820
tgcctgacca ccatctacga tcggctggag caggagcaca acaacctggt gaacgtgccc    2880
ctgtgcgtgg acatgtgcct gaattggctg ctgaacgtgt acgacaccgg caggaccggc    2940
agaatcagag tgctgtcctt caagaccggc atcatcagcc tgtgcaaggc ccacctggag    3000
gataagtacc gctacctgtt caagcaggtg gccagcagca ccggcttctg cgatcagagg    3060
agactgggcc tgctgctgca cgatagcatc cagatcccta ggcagctggg cgaagtggcc    3120
agctttggcg gcagcaacat cgagccctct gtgaggagct gcttccagtt cgccaacaac    3180
aagcccgaga tcgaggccgc cctgttcctg gattggatga ggctggagcc ccagagcatg    3240
```

-continued

```
gtgtggctgc ctgtgctgca cagagtggcc gccgccgaga ccgccaagca ccaggccaag    3300
tgcaacatct gcaaggagtg ccccatcatc ggcttccggt acaggagcct gaagcacttc    3360
aactacgaca tctgccagag ctgctttttc agcggcagag tggccaaggg ccacaagatg    3420
cactacccca tggtggagta ctgcaccccc accacctccg gcgaggatgt gagagacttc    3480
gccaaagtgc tgaagaataa gttccggacc aagcggtact ttgccaagca ccccaggatg    3540
ggctacctgc ccgtgcagac cgtgctggag ggcgacaaca tggagaccga caccatgtga    3600
tgatga                                                                3606
```

```
<210> SEQ ID NO 8
<211> LENGTH: 501
<212> TYPE: PRT
<213> ORGANISM: homo sapiens

<400> SEQUENCE: 8

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
        50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
            115                 120                 125

Pro Gly Gly Lys Ala Pro Pro Lys Ala Gly Ser Val Pro Ser Ser Phe
        130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
                180                 185                 190

Lys Leu Glu Ala Gly Leu Ala Asn Thr Ile Thr Ser Phe Ile Asp Lys
            195                 200                 205

Gly Gln Asp Asp Arg Gly Pro Val Val Arg Lys Gln Arg Tyr Val Phe
        210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
            275                 280                 285

Ser Gly Trp Glu Val Phe Asp Ile Trp Lys Leu Phe Arg Asn Phe Lys
        290                 295                 300
```

-continued

```
Asn Ser Ala Gln Leu Cys Leu Glu Leu Glu Ala Trp Glu Arg Gly Arg
305             310             315             320

Ala Val Asp Leu Arg Gly Leu Gly Phe Asp Arg Ala Ala Arg Gln Val
            325             330             335

His Glu Lys Ala Leu Phe Leu Val Phe Gly Arg Thr Lys Lys Arg Asp
            340             345             350

Leu Phe Phe Asn Glu Ile Lys Ala Arg Ser Gly Gln Asp Asp Lys Thr
        355             360             365

Val Tyr Glu Tyr Leu Phe Ser Gln Arg Arg Lys Arg Arg Ala Pro Leu
    370             375             380

Ala Thr Arg Gln Gly Lys Arg Pro Ser Lys Asn Leu Lys Ala Arg Cys
385             390             395             400

Ser Arg Lys Ala Leu His Val Asn Phe Lys Asp Met Gly Trp Asp Asp
            405             410             415

Trp Ile Ile Ala Pro Leu Glu Tyr Glu Ala Phe His Cys Glu Gly Leu
            420             425             430

Cys Glu Phe Pro Leu Arg Ser His Leu Glu Pro Thr Asn His Ala Val
            435             440             445

Ile Gln Thr Leu Met Asn Ser Met Asp Pro Glu Ser Thr Pro Pro Thr
    450             455             460

Cys Cys Val Pro Thr Arg Leu Ser Pro Ile Ser Ile Leu Phe Ile Asp
465             470             475             480

Ser Ala Asn Asn Val Val Tyr Lys Gln Tyr Glu Asp Met Val Val Glu
            485             490             495

Ser Cys Gly Cys Arg
            500
```

<210> SEQ ID NO 9
<211> LENGTH: 120
<212> TYPE: PRT
<213> ORGANISM: homo sapiens

<400> SEQUENCE: 9

```
Ala Pro Leu Ala Thr Arg Gln Gly Lys Arg Pro Ser Lys Asn Leu Lys
1               5               10              15

Ala Arg Cys Ser Arg Lys Ala Leu His Val Asn Phe Lys Asp Met Gly
            20              25              30

Trp Asp Asp Trp Ile Ile Ala Pro Leu Glu Tyr Glu Ala Phe His Cys
        35              40              45

Glu Gly Leu Cys Glu Phe Pro Leu Arg Ser His Leu Glu Pro Thr Asn
    50              55              60

His Ala Val Ile Gln Thr Leu Met Asn Ser Met Asp Pro Glu Ser Thr
65              70              75              80

Pro Pro Thr Cys Cys Val Pro Thr Arg Leu Ser Pro Ile Ser Ile Leu
            85              90              95

Phe Ile Asp Ser Ala Asn Asn Val Val Tyr Lys Gln Tyr Glu Asp Met
            100             105             110

Val Val Glu Ser Cys Gly Cys Arg
        115             120
```

<210> SEQ ID NO 10
<211> LENGTH: 120
<212> TYPE: PRT
<213> ORGANISM: artificial
<220> FEATURE:
<223> OTHER INFORMATION: rhGDF5

-continued

<400> SEQUENCE: 10

Ala Pro Ser Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
                100                 105                 110

Val Val Glu Ser Cys Gly Cys Arg
        115                 120

<210> SEQ ID NO 11
<211> LENGTH: 25
<212> TYPE: DNA
<213> ORGANISM: artificial
<220> FEATURE:
<223> OTHER INFORMATION: antisense oligonucleotide

<400> SEQUENCE: 11
ggccaaacct cggcttacct gaaat                                          25

<210> SEQ ID NO 12
<211> LENGTH: 20
<212> TYPE: DNA
<213> ORGANISM: artificial
<220> FEATURE:
<223> OTHER INFORMATION: Primer sequence (PO fw, mouse)

<400> SEQUENCE: 12
ctccaagcag atgcagcaga                                                20

<210> SEQ ID NO 13
<211> LENGTH: 20
<212> TYPE: DNA
<213> ORGANISM: artificial
<220> FEATURE:
<223> OTHER INFORMATION: Primer sequence (PO rv, mouse)

<400> SEQUENCE: 13
atagccttgc gcatcatggt                                                20

<210> SEQ ID NO 14
<211> LENGTH: 20
<212> TYPE: DNA
<213> ORGANISM: artificial
<220> FEATURE:
<223> OTHER INFORMATION: Primer sequence (Id-2 fw, mouse)

<400> SEQUENCE: 14
ctccaagctc aaggaactgg                                                20

<210> SEQ ID NO 15
<211> LENGTH: 20
<212> TYPE: DNA
<213> ORGANISM: artificial

-continued

```
<220> FEATURE:
<223> OTHER INFORMATION: Primer sequence (Id-2 rv, mouse)

<400> SEQUENCE: 15
attcagatgc ctgcaaggac                                                    20

<210> SEQ ID NO 16
<211> LENGTH: 20
<212> TYPE: DNA
<213> ORGANISM: artificial
<220> FEATURE:
<223> OTHER INFORMATION: Primer sequence (Id-1 fw, mouse)

<400> SEQUENCE: 16
agtgagcaag gtggagatcc                                                    20

<210> SEQ ID NO 17
<211> LENGTH: 18
<212> TYPE: DNA
<213> ORGANISM: artificial
<220> FEATURE:
<223> OTHER INFORMATION: Primer sequence (Id-1 rv, mouse)

<400> SEQUENCE: 17
gatcgtcggc tggaacac                                                      18

<210> SEQ ID NO 18
<211> LENGTH: 22
<212> TYPE: DNA
<213> ORGANISM: artificial
<220> FEATURE:
<223> OTHER INFORMATION: Primer sequence (Gdf5 fw, mouse)

<400> SEQUENCE: 18
atgctgacag aaagggaggt aa                                                 22

<210> SEQ ID NO 19
<211> LENGTH: 22
<212> TYPE: DNA
<213> ORGANISM: artificial
<220> FEATURE:
<223> OTHER INFORMATION: Primer sequence (Gdf5 rv, mouse)

<400> SEQUENCE: 19
gcactgatgt caaacacgta cc                                                 22
```

COMBINED THERAPY FOR MUSCULAR DISEASES

CROSS-REFERENCE TO RELATED APPLICATIONS

This application is the U.S. national phase of International Application No. PCT/EP2020/081200 filed Nov. 5, 2020 which designated the U.S. and claims priority to EP Patent Application No. 19207561.2 filed Nov. 6, 2019, the entire contents of each of which are hereby incorporated by reference.

REFERENCE TO A SEQUENCE LISTING

This application contains a Sequence Listing, which is submitted electronically via EFSWeb in ASCII format with a file name 3665-378_Sequence_Listing.txt, creation date of May 5, 2022, and a size of 19 KB. This sequence listing submitted is part of the specification and is herein incorporated by reference in its entirety.

FIELD OF THE INVENTION

The present invention relates to the treatment of muscular diseases.

BACKGROUND OF THE INVENTION

Muscular diseases are disorders affecting muscles, which can cause weakness, pain, or even paralysis.

Among muscular diseases, muscular dystrophy is a group of muscular diseases that results in increasing weakening and breakdown of skeletal muscles over time. In particular, dystrophinopathies are pathologies caused by anomalies in the DMD gene that encodes a subsarcolemmal protein called dystrophin. With regard to the large deletions, the most frequent genetic alteration, the severity of the phenotype is primarily conditioned by the impact of the mutation on the protein reading frame of the dystrophin transcript. The dystrophin structure (central rod-domain made of 24 spectrin-like repeats) tolerates large internal deletions (1) which led to the development of two main therapeutic strategies: classical gene therapy with transfer of functional micro-dystrophin cDNAs in muscles, and targeted exon skipping. We also have previously shown in WO2016198676 that a two-step combination therapy of a muscular dystrophy is advantageous over treatment strategies known in the prior art. This combination therapy comprises the administration of an isolated AON suitable for inducing exon-skipping within a dystrophin pre-mRNA and inducing muscle cells to produce an mRNA transcript that encodes a functional dystrophin protein. In a second step, the therapy comprises administering to the same subject at least one viral vector encoding a Duchenne muscular dystrophy therapeutic product. The viral vector (or therapeutic viral vector) is designed for restoring a dystrophin function in a muscle cell. For example, the at least one viral vector able to restore a dystrophin function in the muscle cell is a viral vector either (i) coding for an antisense oligonucleotide (which is also referred to as "AON-coding virus" in the following description) able to induce exon-skipping within a dystrophin pre-mRNA and inducing muscle cells to produce an mRNA transcript that encodes a functional dystrophin protein, (ii) designed to introduce into the muscle cell means for correcting the dystrophin gene in the genome of said muscle cell, such as genome-editing means implementing one or more endonucleases specific for the dystrophin gene, or (iii) coding a functional dystrophin protein.

It is herein shown that such strategies, and other strategies for treating muscular dystrophies but also other muscular diseases, benefit from the administration of a GDF5 pathway-activating substance.

SUMMARY OF THE INVENTION

In a first aspect, the present invention relates to a GDF5 pathway-activating substance for use in a method for treating a muscular disease by gene therapy, wherein the GDF5 pathway-activating substance is used in combination with another active ingredient suitable for the treatment of the muscular disease.

In a second aspect, the invention relates to a kit comprising (i) a GDF5 pathway-activating substance and (ii) an active ingredient suitable for the treatment of a muscular diseases/. The kit of the present invention is useful for implementing the therapeutic methods described herein.

DETAILED DESCRIPTION OF THE INVENTION

The present inventors herein show that GDF5 overexpression leads to muscle mass increase in both denervated and innervated muscles. This observation can advantageously be implemented in a method for the treatment of a muscular disease, wherein an active ingredient suitable to treat the muscular diseases is administered to a subject in need thereof, and wherein a GDF5 pathway-activating substance is used in combination to said active ingredient to increase or stabilize muscle mass and/or muscle function.
GDF5 Pathway-Activating Substance In a particular embodiment, the GDF5 pathway-activating substance is a GDF5 peptide, in particular synthetic or recombinant GDF5, more particularly recombinant GDF5, such as recombinant human GDF5. Unprocessed wild-type human GDF-5 (Uniprot Accession No. P43026) has the following sequence:

```
                                    (SEQ ID NO: 8)
MRLPKLLTFLLWYLAWLDLEFICTVLGAPDLGQRPQGTRPGLAKAEAKE

RPPLARNVFRPGGHSYGGGATNANARAKGGTGQTGGLTQPKKDEPKKLP

PRPGGPEPKPGHPPQTRQATARTVTPKGQLPGGKAPPKAGSVPSSFLLK

KAREPGPPREPKEPFRPPPITPHEYMLSLYRTLSDADRKGGNSSVKLEA

GLANTITSFIDKGQDDRGPVVRKQRYVFDISALEKDGLLGAELRILRKK

PSDTAKPAAPGGGRAAQLKLSSCPSGRQPASLLDVRSVPGLDGSGWEVF

DIWKLFRNFKNSAQLCLELEAWERGRAVDLRGLGFDRAARQVHEKALFL

VFGRTKKRDLFFNEIKARSGQDDKTVYEYLFSQRRKRRAPLATRQGKRP

SKNLKARCSRKALHVNFKDMGWDDWIIAPLEYEAFHCEGLCEFPLRSHL

EPTNHAVIQTLMNSMDPESTPPTCCVPTRLSPISILFIDSANNVVYKQY

EDMVVESCGCR
```

SEQ ID NO:8 comprises a signal peptide at amino acid positions 1-27, a propeptide at amino acid positions 28-381 and a part, underlined in the sequence provided above, corresponding to the mature peptide at amino acid positions 382-501.

The mature peptide thus has a sequence as shown in SEQ ID NO:9 below:

(SEQ ID NO: 9)
```
APLATRQGKRPSKNLKARCSRKALHVNFKDMGWDDWIIAPLEYEAFHCE
GLCEFPLRSHLEPTNHAVIQTLMNSMDPESTPPTCCVPTRLSPISILFI
DSANNVVYKQYEDMVVESCGCR.
```

Other recombinant human GDF5 are commercially available, such as the protein having the sequence shown in SEQ ID NO:3, which is available from Thermo Fischer (catalog No. RP-8663):

(SEQ ID NO: 10)
```
APSATRQGKRPSKNLKARCSRKALHVNFKDMGWDDWIIAPLEYEAFHCE
GLCEFPLRSHLEPTNHAVIQTLMNSMDPESTPPTCCVPTRLSPISILFI
DSANNVVYKQYEDMVVESCGCR
```

In the context of the present invention, the peptide shown in SEQ ID NO:9 or SEQ ID NO:10 may be referred to as "a reference recombinant human GDF5".

According to another particular embodiment, the GDF5 pathway-activating substance is a functional derivative of a GDF5 peptide. A functional derivative according to the invention is a peptide having at least one, in particular all, activity of a reference peptide. In the context of the present invention, a functional variant of a GDF5 peptide may have its ability to induce alkaline phosphatase production by ATDC5 mouse chondrogenic cells (Nakamura, K. et al. (1999) Exp. Cell Res. 250:351.) with an ED50 from 0.01 to 10 µg/mL, such as from 0.2 to 4 µg/mL, for example from 0.2 to 1.2 µg/mL. In particular, a functional variant of a GDF5 peptide is a peptide that may treat or prevent sarcopenia in an animal model of the condition, as provided in the experimental part of this application, or in a human subject. GDF5 signaling may also be evaluated by measuring SMAD 1/5/8 phosphorylation, SMAD 4 nuclear translocation and Id-1 transcription as provided in the experimental part below. The activity of the functional variant may be of at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or at least 100% of the activity of the reference GDF5 peptide. In a particular embodiment, the functional peptide as an activity greater than the activity of the reference GDF5 peptide, such as an activity of at least 105%, 110%, 115%, 120%, 125%, 130%, 135%, 140%, 145%, or of at least 150% of the activity of the reference GDF5 peptide. In addition, according to the invention, a functional variant of a GDF5 peptide has at least 80% sequence identity to a reference GDF5 amino acid sequence, in particular at least 81%, 82%, 83%, 84%, 85%, 86%, 87%, 88%, 89%, 90%, 91%, 92%, 93%, 94%, 95%, 96%, 97%, 98% or at least 99% sequence identity to a reference human recombinant GDF5. For example, a functional variant of a GDF5 peptide may comprise from 1 to 20 amino acid modifications (i.e. amino acid addition, deletion or substitution) as compared to a reference recombinant human GDF5, such as from 1 to 15 amino acid modifications, in particular from 1 to 10 amino acid modifications, more particularly from 1 to 6 amino acid modifications, even more particularly 1, 2, 3, 4, 5 or 6 amino acid modifications as compared to a reference recombinant human GDF5. Such a functional variant of recombinant human GDF5 may be a natural variant of GDF5. In a particular aspect, the functional variant is an optimized GDF5 peptide. Optimization may include different changes in the peptide, such as amino acid modifications as provided above, glycosylation, acetylation, phosphorylation and the like, or inclusion of at least one D-amino acid, such as at least 2, at least 3, at least 4 or at least 5 D amino acids. In another aspect, the GDF5 peptide comprises at least one non-natural amino acid, included by insertion, appendage, or substitution for another amino acid of the GDF5 sequence. In yet another aspect, recombinant GDF5 may be fused to another moiety, such as another peptide moiety. Such other moiety may, for example, stabilize the peptide.

In another particular embodiment, the substance is a functional variant of a GDF5 peptide corresponding to the GDF5-related proteins as described in WO201308649, having an increased affinity for the BMP receptor IB (BMPR-IB) and/or a reduced affinity for the BMP receptor IA (BMPR-IA). In a particular embodiment, the protein is derived from human wild-type GDF5. In a particular embodiment, the GDF5-related protein is obtained by replacing at least one amino acid residue relating to a BMPR-IB and/or BMPR-IA binding site in the amino acid sequence of the GDF-5 peptide, preferably by genetic engineering technology. In a further embodiment, at least one hydrophobic amino acid in the BMPR-IB and/or BMPR-IA binding site the GDF5 peptide is replaced with a hydrophilic or polar amino acid, such as a hydrophilic amino acid residue or polar amino acid residue selected from the group consisting of aspartic acid, glutamic acid, lysine, arginine, histidine, serine and threonine. In an alternative embodiment, at least one hydrophilic or polar amino acid in the BMPR-IB and/or BMPR-IA binding site of the GDF5 peptide is replaced with a hydrophobic amino acid, such as a hydrophobic amino acid selected from the group consisting of alanine, isoleucine, leucine, methionine, phenylalanine, proline, tryptophan, tyrosine, valine. In another alternative embodiment, the GDF5-related protein comprises a conservative substitution of at least one amino acid in the BMPR-IB and/or BMPR-IA binding site of the GDF peptide, in particular wherein a hydrophobic amino acid is replaced by a smaller or lager hydrophobic amino acid or wherein a hydrophilic or polar amino acid is replaced by a smaller or lager hydrophilic or polar amino acid. The regions of GDF-5 related proteins which are involved in binding to BMPR-IA and/or BMPR-IB are well known in the art or can easily be determined using methods that are within common knowledge. Referring to the unprocessed, full-length amino acid sequence of wild-type human GDF5 of SEQ ID NO:8, a particular embodiment provides the replacement of one or more of the following amino acids by any different amino acid:

R399;

any one of F409 to W417, in particular M412, G413, W414, and/or W417;

any one of E 434 to M 456, in particular F435, P436, L437, R438, S439, H440, P443, N445, V448, I449, L452, M453, S455, and/or M456;

S475;

1476;

F478;

any one of K488 to M493, in particular K488, Y490, and/or D492.

In particular embodiments, referring to the unprocessed, full-length amino acid sequence of SEQ ID NO:8, one or more of the following amino acids are replaced by the specified amino acid R399 is replaced by V, L, I, M, F, Y, W, E or D;

M412 is replaced by V, L, I, F, Y, W, H, K or R;

W414 is replaced by R, K, F, Y, H, E or D;

W417 is replaced by R, K, F, Y, H, E or D;

F435 is replaced by V, L, I, M, P, Y, W, H, K or R;

P436 is replaced by V, L, I, M, F, Y or W;

L437 is replaced by D or E;

R438 is replaced by K, D, H, N, M, E, Q, S, T, Y or W;

S439 is replaced by K, D, E, H, R, M, T, N, Q, Y or W;

H440 is replaced by V, I, M, F, Y, W, E or D;

P443 is replaced by V, L, I, M, F, Y, W, A or S;

N445 is replaced by D, Q, H, F, L, R, K, M, S, Y or W;

V448 is replaced by F, L, I, M, P, Y or W;

1449 is replaced by F, L, V, M, P, Y or W;

L452 is replaced by F, I, V, M, P, Y or W;

M456 is replaced by F, I, L, P, Y, W, S, T, N, Q, K or D;

S475 is replaced by M, T, N, Q, Y or W;

K488 is replaced by R, M, S, T, N, Q, Y or W;

Y490 is replaced by E, H, K, R, Q, F, T, M, S, N, Q or W;

D492 is replaced by G, E, M, S, T, N, Q, Y, W, H, K or R;

1476 is replaced by G, A, V, L, M, F, Y or W;

F478 is replaced by G, A, V, L, I, Y or W.

In another particular embodiment, referring to the unprocessed, full-length amino acid sequence of SEQ ID NO:8, one or more of the following amino acids are replaced by the specified amino acid:

R399 is replaced by M or E;

W414 is replaced by R;

W417 is replaced by R or F;

R438 is replaced by K;

S439 is replaced by K or E;

1449 is replaced by V.

The corresponding positions in the mature peptides (such as in SEQ ID NO:9 or SEQ ID NO:10) will easily be derived from the above information regarding unprocessed, full-length wild-type human GDF-5.

In a particular embodiment of the invention, the substance is a GDF5 peptide whose amino acid consists of SEQ ID NO:9 or SEQ ID NO:10. In another particular embodiment, the substance is a GDF5 peptide whose amino sequence consists of SEQ ID NO:9 or SEQ ID NO:10, with the addition of a methionine residue at its N-terminal end. In another embodiment, the substance is a GDF5 peptide whose amino acid consists of SEQ ID NO:9 or SEQ ID NO:10, wherein the first alanine residue is replaced by a methionine residue.

In a further particular embodiment, the GDF5 pathway-activating substance is a substance inducing the CaVβ1-E/GDF5 axis. In this embodiment, a variant comprises the use of a substance that is a small chemical molecule. In a non-limiting variant of this embodiment, the GDF5 pathway-activating substance is an inhibitor of NRSF (Neuron-Restrictive Silencer Factor; also referred to as REST or RE1-Silencing Transcription Factor).

In a particular embodiment, the GDF5 pathway-activating substance is the NRSF inhibitor is valproic acid. In a further particular embodiment, the GDF5 pathway-activating substance is selected from the NRSF inhibitors disclosed in Charbord et al., Stem Cells. 2013 Sep; 31(9):1816-28, in particular the 2-(2-Hydroxy-phenyl)-1H-benzoimidazole-5-carboxylic acid allyloxy-amide (X5050), 2-Thiophen-2-yl-1H-benzoimidazole-5 -carboxylic acid (2-ethyl-hexyl)-amide (X5917), 3-[1-(3-Bromo-phenyl)-3,5-dimethyl-1H-pyrazol-4-yl]-1-{4-[5-(morpholine-4-carbonyl)-pyridin-2-yl]-2-phenyl-piperazin-1-yl}-propan-1-one (X38210) or 3-[1-(2,5-Difluoro-phenyl)-3,5-dimethyl-1H-pyrazol-4-yl]-1-{4-[5-(morpholine-4-carbonyl)-pyridin-2-yl]-2-phenyl-piperazin-1-yl}-propan-1one (X3 8207) molecule disclosed therein, more particularly the X5050 molecule disclosed therein.

In yet another embodiment, the GDF5 pathway-activating substance is a vector comprising a nucleic acid encoding GDF5, such as human GDF5 or a functional variant thereof.

6

In a particular embodiment, the vector is a plasmid or viral vector, such as an adenoviral vector or an adeno-associated virus (AAV) vector. According to a particular embodiment, the viral vector is suitable for transducing muscle and/or neuronal cells. In a more particular embodiment such viral vector suitable for transducing muscle and/or neuronal cells is an AAV vector, such as an AAV vector having an AAV2/2, AAV2/6, AAV2/8, AAV2/9 or AAV2/10 capsid. In a further particular embodiment. The GDF5 coding sequence may be under the control of regulatory sequences such as promoters, enhancers, repressors and polyadenylation signals. In a particular embodiment, the vector comprises an expression cassette, comprising, in this order, a promoter, the GDF5 coding sequence and a polyadenylation signal. The promoter may be ubiquitous or tissue-selective. In a particular embodiment, the promoter is the natural promoter of the GDF5 gene, such as the promoter of the human GDF5 gene.

In another particular embodiment, the GDF5 pathway-activating substance is a substance that increases the activity or the expression of GDF5.

In a further embodiment, the GDF5 pathway-activating substance is a vector comprising a nucleic acid encoding CaVβ1-E, such as human CaVβ1-E. In a particular embodiment, the vector is a plasmid or viral vector, such as an adenoviral vector or an adeno-associated virus vector. Accordingly, the present invention also relates to a vector, such as a viral vector, for example an adenoviral or AAV vector as described above, comprising CaVβ31-E coding sequence. The CaVβ1-E coding sequence may be under the control of regulatory sequences such as promoters, enhancers, repressors and polyadenylation signals. In a particular embodiment, the vector comprises an expression cassette, comprising, in this order, a promoter, the CaVβ1-E coding sequence and a polyadenylation signal. The promoter may be ubiquitous or tissue-selective. In a particular embodiment, the promoter is the natural promoter of the CaVβ1-E gene, such as the promoter of the human CaVβ1-E gene.

In a particular embodiment, the GDF5 pathway-activating substance is either (i) a vector comprising a nucleic acid encoding GDF5, such as human GDF5 or a functional variant thereof, such as an AAV vector, or (ii) recombinant GDF5, such as recombinant human GDF5 or a functional variant thereof, as disclosed above. In yet another particular embodiment, the GDF5 pathway-activating substance is recombinant GDF5, such as recombinant human GDF5 or a functional variant thereof In a particular embodiment, the GDF5 pathway-activating substance is administered separately, sequentially or simultaneously with the other active ingredient(s). For example, administrations can be simultaneous (for example, because the substance and ingredient(s) are comprised within the same composition, or because two different compositions each comprising the substance and the active ingredient(s), respectively, are administered at the same time) or are several hours, days, weeks or months apart. In another particular embodiment, the GDF5 pathway-activating substance is a vector, such as a plasmid vector or a viral vector, in particular an AAV vector, and said substance is administered only once. In yet a further embodiment, the GDF5 pathway-activating substance is a recombinant protein as described above in each of its embodiments, and said recombinant GDF5 protein may be administered only once, for example before, during or after administration of the other active ingredient(s) to increase muscle mass and/or function before, during or after the active ingredient can act. In another embodiment, the GDF5 pathway-activating substance is a recombinant protein as described above in each of its embodiments, and said recombinant GDF5 protein may be administered several times, to maintain suitable muscle mass and/or function throughout the treatment protocol. For example, administration of the GDF5 recombinant protein may be carried out at least once a year, such as at least once every 6 months, such as at least once a quarter, such as at least once a month, such as at least once a week, such as at least once a day.

Muscular Diseases and Active Ingredients Suitable for Their Treatment

The present invention relates to the treatment of a muscular disease. Among muscular diseases that can benefit from the invention are genetic diseases. In a particular embodiment, the muscular disease is a neuromuscular disease or a musculoskeletal disease.

In a particular embodiment, the muscular disease is a motor neuron disease, such as amyotrophic lateral sclerosis (ALS) or spinal muscular atrophy (SMA).

In a particular embodiment, the invention relates to the treatment of ALS, wherein the active ingredient suitable for the treatment of ALS is an AON targeting human SOD 1 pre-mRNA, wherein said AON is suitable to induce exon-skipping in said pre-mRNA. One skilled in the art knows what strategies are relevant to the treatment of ALS. For example, one can refer to the disclosure of WO2016016449. In a particular embodiment, the AON is encoded by a nucleotide sequence of interest introduced within a vector, such as a plasmid or viral vector, for example an AAV vector. General information useful for the design of AONs is available to those skilled in the art, and provided below with respect to AONs targeting dystrophin pre-mRNA, the same principles applying to the design of AONs targeting SOD 1 pre-mRNA.

In a further particular embodiment, the invention relates to the treatment of spinal muscular atrophy, wherein the active ingredient is a vector, such as a plasmid or viral vector, for example an AAV vector, comprising a gene encoding for a survival of motor neuron protein, such as the SMN1 or SMN2 gene.

In yet another embodiment, the muscular disease is an atrophic muscular disorder, such as a muscular dystrophy. Non-limiting examples of muscular dystrophies that can be treated according to the invention include distal myopathies, Glycogen Storage Disease Type VII, limb-girdle muscular dystrophies, Duchenne muscular dystrophy (DMD), Becker muscular dystrophy, Emery-Dreifuss muscular dystrophy, facioscapulohumeral muscular dystrophy, oculopharyngeal muscular dystrophy and myotonic dystrophy.

In a particular embodiment, the muscular disease to be treated is a Duchenne muscular dystrophy. In a further particular embodiment, the active ingredients for the treatment of DMD are those disclosed in WO2016198676, wherein a two-step combination therapy of a muscular dystrophy is implemented. In this embodiment, first is administered an isolated AON suitable for inducing exon-skipping within a dystrophin pre-mRNA and inducing muscle cells to produce an mRNA transcript that encodes a functional dystrophin protein. In a second step, the same subject is administered with at least one viral vector encoding a DMD therapeutic product. The viral vector (or therapeutic viral vector) is designed for restoring a dystrophin function in a muscle cell. For example, the at least one viral vector able to restore a dystrophin function in the muscle cell is a viral vector either:

(i) coding for an antisense oligonucleotide (which is also referred to as "AON-coding virus" in the following description) able to induce exon-skipping within a dystrophin pre-mRNA and inducing muscle cells to produce an mRNA transcript that encodes a functional dystrophin protein, (ii) designed to introduce into the muscle cell means for correcting the dystrophin gene in the genome of said muscle cell, such as genome-editing means implementing one or more endonucleases specific for the dystrophin gene, or (iii) coding a functional dystrophin protein.

The term "antisense oligonucleotide" and "AON" are used interchangeably and refer to a single stranded nucleic acid sequence, e.g. a DNA or RNA sequence, which is complementary to a part of a pre-mRNA coding the dystrophin protein and is thus able to form, by Watson-Crick base pairing, to a heteroduplex within the target sequence. In particular, the AON of the present invention is designed to block a splice acceptor (SA) site and/or an exon splicing enhancer (ESE) and/or a branch point in the dystrophin pre-mRNA and/or a splice donor (SD) site and/or any sequence which could modulate pre-mRNA splicing, i.e. it is designed to be complementary to a part of the dystrophin pre-mRNA comprising an SA, an ESE, a branch point sequence, an SD, and/or any sequence which could modulate pre-mRNA splicing (14,15). In a particular embodiment, the targeted sequence within the dystrophin pre-mRNA may include a 3' or 5' splice site of a pre-mRNA, or a branch point. The target sequence may be within an exon or within an intron or overlapping an intron-exon or exon-intron junction. The target sequence for a splice site may include an mRNA sequence having its 5' end 1 to about 50 base pairs downstream of a normal splice acceptor junction in a preprocessed mRNA. A preferred target sequence for a splice is any region of a pre-mRNA that includes a splice site and/or is contained entirely within an exon coding sequence and/or spans a splice acceptor and/or donor site. Of course, the target sequence may include several of these sequences that can modulate pre-mRNA splicing, and several such target sequences can be combined to achieve the desired effect.

Tools are available for identifying SA, ESE, SD and branch point sequences in a pre-mRNA of interest. As is well known by those skilled in the art, SA are conserved sequences, they are at the 3' end of the intron and terminate the intron with an almost invariant AG sequence. SD are conserved sequences, they are at the 5' end of the intron and start the intron with an almost invariant GT sequence. In addition, ESE motifs may be predicted on the exon sequence intended to be skipped using the ESEfinder software tool (rulai.cshl.edu/cgi-bin/tools/ESE3/esefinder.cgi?process=home). Design of the AON can then be carried out following the rules published in Aartsma-Rus et al. (16).

The AON of the invention is designed to complement suitable sequences within the dystrophin pre-mRNA which are required for correct splicing of the targeted exon, thereby blocking splicing reactions that would incorporate the targeted exon into mature mRNA.

The mutated human dystrophin genes express no measurable dystrophin at all in muscles of Duchenne muscular dystrophy patients. To remedy this condition, the antisense oligonucleotides of the present invention typically hybridize to selected regions of a pre-mRNA of a mutated human dystrophin gene, induce exon skipping in dystrophin mRNA, and thereby allow muscle cells to produce an mRNA transcript that encodes a functional dystrophin protein. Exon skipping strategy converts an out-of-frame mutation into an in-frame mutation leading to an internally deleted but partially functional dystrophin. Therefore, depending on the skipped exon(s), the rescued proteins will at best improve dystrophic phenotypes toward milder Becker-like phenotypes. In certain embodiments, the resulting dystrophin protein is not necessarily the "wild-type" form of dystrophin, but is rather a truncated, yet functional or semi-functional, form of dystrophin. By increasing the levels of functional dystrophin protein in muscle cells, these and related embodiments may be useful in the prophylaxis and treatment of Duchenne muscular dystrophy. The combined therapy described herein provides significant and practical advantages over alternate methods of treating Duchenne muscular dystrophy.

"Exon skipping" refers generally to the process by which an entire exon, or a portion thereof, is removed from a given pre-mRNA, and is thereby excluded from being present in the mature mRNA. Hence, the portion of the protein that is otherwise encoded by the skipped exon is not present in the expressed form of the protein, typically creating an altered, though still functional, form of the protein. In certain embodiments, the exon being skipped is an aberrant exon from the human dystrophin gene, which may contain a mutation or other alteration in its sequence. In certain embodiments, the exon being skipped is any one or more of exons 1-79 of the dystrophin gene, though any one or more of exons 23, 43, 44, 45, 46, 47, 48, 49, 50, 51, 52, 53, 54, and/or 55 of the human dystrophin gene are preferred. Depending of the localization of the DMD patient mutation, one or several exons are chosen to be skipped to restore the dystrophin coding frame leading to an internally deleted but partially functional dystrophin. "Dystrophin" is a rod-shaped cytoplasmic protein, and a vital part of the protein complex that connects the cytoskeleton of a muscle fiber to the surrounding extracellular matrix through the cell membrane. Dystrophin contains multiple functional domains. For instance, dystrophin contains an actin binding domain at about amino acids 14-240 and a central rod domain at about amino acids 253-3040. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Repeats 15 and 16 are separated by an 18 amino acid stretch that appears to provide a major site for proteolytic cleavage of dystrophin. The sequence identity between most repeats ranges from 10-25%. One repeat contains three alpha-helices: 1, 2 and 3. Alpha-helices 1 and 3 are each formed by 7 helix turns, probably interacting as a coiled-coil through a hydrophobic interface. Alpha-helix 2 has a more complex structure and is formed by segments of four and three helix turns, separated by a Glycine or Proline residue. Each repeat is encoded by two exons, typically interrupted by an intron between the nucleic acid position coding amino acids 47 and 48 in the first part of alpha-helix 2. The other intron is found at different positions in the repeat coding region, usually scattered over helix-3. Dystrophin also contains a cystein-rich domain at about amino acids 3080-3360), including a cystein-rich segment (i.e., 15 Cysteins in 280 amino acids) showing homology to the C-terminal domain of the slime mold (Dictyostelium discoideum) alpha-actinin. The carboxy-terminal domain is at about amino acids 3361-3685.

The amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally inherited muscular dystrophies. The DAPC is destabilized when dystrophin is absent, which results in diminished levels of the member proteins, and in turn leads to progressive fibre damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence. The predominant expression of the defective dystrophin protein, or the complete lack of dystrophin or a dystrophin-like protein, leads to rapid progression of muscle degeneration, as noted above. In this regard, a "defective" dystrophin protein may be characterized by the forms of dystrophin that are produced in certain subjects with DMD or BMD, as known in the art, or by the absence of detectable dystrophin.

As used herein, the terms "function" and "functional" and the like refer to a biological, enzymatic, or therapeutic function. A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. As one example, dystrophin-related activity in muscle cultures in vitro can be measured according to myotube size, myofibril organization (or disorganization), contractile activity, and spontaneous clustering of acetylcholine receptors (17). Animal models are also valuable resources for studying the pathogenesis of disease, and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, lnt J Exp Pathol 84: 165-172, 2003). These and other animal models can be used to measure the functional activity of various dystrophin proteins. Included are truncated forms of dystrophin, such as those forms that are produced by certain of the exon-skipping antisense compounds of the present invention.

The isolated AON of the invention may be of any suitable type. Representative AON types include oligodeoxyribonucleotides, oligoribonucleotides, morpholinos (such as phosphorodiamidate morpholino (PMO) or peptide-phosphorodiamidate morpholino (PPMO)), 2'-O-methyl-phosphorothioate (2'OMePS), 2'-O-2-methoxyethyl-antisense oligonucleotides, tricyclo-DNA-antisense oligonucleotides, tricyclo-phosphorothioate DNA oligonucleotides, LNA, small nuclear RNA-modified such as U7-, U1- or U6-modified AONs (or other UsnRNPs), or conjugate products thereof such as peptide-conjugated or nanoparticle-complexed AONs.

In particular, for use in vivo, the AONs may be stabilized, for example via phosphate backbone modifications. For example, stabilized AONs of the instant invention may have a modified backbone, e.g. have phosphorothioate linkages. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AONs also include "Morpholinos" (phosphorodiamidate morpholino oligomers, PMOs), 2'-O-Methyl oligomers, tricyclo-DNAs, tricyclo-DNA-phosphorothioate AON molecules (WO2013/053928) or U small nuclear (sn) RNAs. The latter forms of AONs that may be used to this effect can be coupled to small nuclear RNA molecules such as U1, U6 or U7 (or other UsnRNPs).

In a particular embodiment, the isolated AON used in the present invention is a 2'OMePS oligonucleotide or a PPMO oligonucleotide. Preferably, the AON is a PPMO oligonucleotide.

AONs employed in the practice of the invention are generally from about 10 to about 40 nucleotides in length, and may be for example, about 10, or about 15, or about 20, or about 25, or about 30, or about 35, or about 40 nucleotides or more in length depending on the targeted sequences within the dystrophin pre-mRNA and the AON chemistry.

A representative AON for practice of the invention effects exon 51 skipping or exon 53 skipping of human dystrophin pre-mRNA. In a more particular embodiment, the AON for practice of the invention effects exon 51 skipping of human dystrophin pre-mRNA. In another particular embodiment, the AON for practice of the invention may be CATT-CAACTGTTGCCTCCGGTTCTGAAGGTGTTCTTGTAC (SEQ ID NO:1), effecting exon 53 skipping of human dystrophin pre-mRNA.

Of course, any AON having the properties described above may be used in the practice of the present invention.

In an embodiment, the isolated AON of the invention has the sequence shown in SEQ ID NO:1 and is a PPMO oligonucleotide.

For stable and efficient in vivo delivery, the isolated AONs used in the practice of the present invention may also be fused or co-administrated to any cell-penetrating peptides and to signal peptides mediating protein secretion. Cell-penetrating peptides can be RVG peptides (18), PiP (19) such as Pip6a-PMO (20), P28 (21), or protein transduction domains like TAT (22) or VP22 (23). In a particular embodiment, the isolated AON is a PPMO oligonucleotide, i.e. a PMO oligonucleotide fused to a peptide moiety, more particularly a Pip6a-PMO, even more particularly a Pip6a-PMO. In a particular embodiment, the PPMO oligonucleotide moiety comprises or consists of the sequence shown in SEQ ID NO:1. In a further particular embodiment, the isolated AON is a Pip6a-PMO whose oligonucleotide moiety comprises or consists of the sequence shown in SEQ ID NO:1.

Furthermore, the isolated AON used in the practice of the invention may be administered as a composition further comprising a pharmaceutically acceptable carrier and a reagent that improves oligonucleotide delivery efficiency. Such reagent may include, without limitation, F127 (24).

In a particular embodiment of the invention, the isolated AON of the invention is capable of inducing functional dystrophin expression of at least 10%, preferably of at least 20%, preferably of at least 30%, preferably of at least 40%, preferably 50%, more preferably at least 51%, 52%, 53%, 54%, 55% or at least 56%, as compared to the normal expression level of wild-type dystrophin. Of course, higher functional dystrophin expression is also preferable, such as an expression of at least 60%, 70%, 80% or even of at least 90%, as compared to the normal expression level of wild-type dystrophin.

In the second step of the method invention, a viral vector coding a therapeutic product is also administered to the same patient in need of the treatment. In the context of the present invention, the therapeutic product is able to restore a dystrophin function in a muscle cell in need thereof.

In a particular embodiment, the viral vector coding a therapeutic product is an AON-coding virus. The AON coded by this virus is as defined above, and is able to induce exon-skipping within a dystrophin pre-mRNA and to induce muscle cells to produce an mRNA transcript that encodes a functional dystrophin protein.

In another specific embodiment, the viral vector, or several viral vectors, encodes means for correcting the dystrophin gene in the genome of a muscle cell. In this embodiment, the viral vector able to restore dystrophin function in a muscle cell is designed for correcting a mutant dystrophin gene in a subject by introducing into the genome of said cell a genome-editing system. For example, a site-specific nuclease may be encoded by the viral vector, which may restore the expression of a full-functional or partially-functional dystrophin protein with a repair template or donor DNA, which can replace the entire dystrophin gene or the region containing the mutation. The site-specific nuclease may be used to introduce site-specific double strand breaks at targeted genomic loci. Site-specific double-strand breaks are created when the site-specific nuclease binds to a target DNA sequence, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway. This embodiment may comprise introducing into the muscle cell a genome-editing means implementing one or more endonucleases (for example one or more meganuclease(s), TALEN(s), ZFN(s) or a CRISPR/Cas9 endonuclease) specific for the dystrophin gene and one or more repair matrices. Such systems are described and known to those skilled in the art, for example in WO011036640, WO13163628, WO14009567 and WO14197748.

In another embodiment, the therapeutic product coded by the viral vector is a functional dystrophin. As mentioned above, a "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. The functional dystrophin protein may be a truncated dystrophin protein, such as a mini- or micro-dystrophin. Such mini- and micro-dystrophin are known in the art, for example in WO02/29056, WO01/83695, WO08/088895 and Foster et al., 2008 (37). In a particular embodiment, the micro-dystrophin is a ΔAAB/R3-R18/ΔCT or ΔR4-R23/ΔCT micro-dystrophin (more particularly a ΔR4-R23/ΔCT micro-dystrophin), such as the ΔAB/R3-R18/ΔCT or ΔR4-R23/ΔCT micro-dystrophin described in Foster et al., 2008, more particularly the ΔR4-R23/ΔCT micro-dystrophin. In a further particular embodiment, the mini- or micro-dystrophin coding gene is codon-optimized. In a further particular embodiment, the mini- or micro-dystrophin coding gene is codon optimized and encodes the ΔAB/R3-R18/ΔCT or ΔR4-R23/ΔCT micro-dystrophin, in particular the ΔR4-R23/ΔCT micro-dystrophin described in Foster et al., 2008. The corresponding coding sequences are shown in SEQ ID NO: 6 and 7 respectively.

Adeno-associated viral vector (AAV)-mediated delivery of microdystrophins into dystrophin-deficient mice with DMD has shown remarkable efficiency (25, 26, 27) which has led to the initiation of an early-phase clinical trial (28).

Viral vectors include, but are not limited to, non-integrating viral vectors (or vectors integrating the genome of the target cell with low efficacy) such as episomally-maintained vectors, including adenoviruses; parvoviruses such as adeno-associated viruses; SV40-type viruses. One can readily employ other vectors not named but known in the art. Among the vectors that have been validated for clinical applications and that can be used to deliver the antisense sequences AAVs show a greater potential for exon skipping strategy.

In a preferred embodiment, the viral vector is a parvovirus, in particular an AAV vector. The parvovirus Adeno-Associated Virus (AAV) is a dependent virus that is naturally defective for replication and which is able to integrate into the genome of the infected cell to establish a latent infection. The last property appears to be unique among mammalian viruses because the integration occurs at a specific site in the human genome, called AAVS1, located on chromosome 19 (19q13.3-qter). AAV-based recombinant vectors lack the Rep protein and integrate with low efficacy and are mainly present as stable circular episomes that can persist for months and maybe years in the target cells. Therefore AAV has aroused considerable interest as a potential vector for human gene therapy. Among the favorable properties of the virus are its lack of association with any human disease and the wide range of cell lines derived from different tissues that can be infected. Actually 12 AAV serotypes (AAV1 to 12) and up to 120 variants are known (29; 30), each with different tissue tropisms. Accordingly, the present invention relates to an AAV vector coding the AON described above, targeting a dystrophin pre-mRNA and adapted to induce exon-skipping in said human pre-mRNA and to induce the production of a functional dystrophin protein in muscle cells. According to a particular embodiment, the AAV genome is derived from an AAV1, 2, 3, 4, 5, 6, 7, 8, 9, 10, 11 or 12 serotype. In a preferred embodiment, the AAV capsid is derived from an AAV1, 2, 3, 4, 5, 6, 7, 8, 9, 10, 11 or 12 serotype or AAV variants. In a further particular embodiment, the AAV vector is a pseudotyped vector, i.e. its genome and capsid are derived from AAVs of different serotypes. For example, the pseudotyped AAV vector may be a vector whose genome is derived from the AAV2 serotype, and whose capsid is derived from the AAV1, 3, 4, 5, 6, 7, 8, 9, 10, 11 or 12 serotype AAVs or AAV variants. In addition, the genome of the AAV vector may either be a single stranded or self-complementary double-stranded genome (31). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers.

Preferably, the AAV vector implemented in the practice of the present invention is a vector targeting muscle cells. In particular, AAV1, 6, 8 and 9 exhibit a high tropism for striated muscles (Zincarelli Mol Ther. 2008; Schultz Mol Ther. 2008) and are particularly preferred. In a preferred embodiment, the AAV vector has an AAV1, 6, 8 or 9 capsid, this vector being optionally pseudotyped.

In a particular embodiment, the AON coded by the AON-coding vector as described above is linked to a small nuclear RNA molecule such as a U1, U2, U6, U7 or any other small nuclear RNA (snRNA), or chimeric small nuclear RNA (32; 33). Information on U7 modification can in particular be found in Goyenvalle, et al. (34); WO2011/

113889; and WO2006/021724. In a particular embodiment, the U7 cassette described by D. Schumperli is used (35). It comprises the natural U7-promoter (position −267 to +1), the U7smOpt snRNA and the downstream sequence down to position 116. The 18 nt natural sequence complementary to histone pre-mRNAs in U7 snRNA is replaced by one or two (either the same sequence used twice, or two different sequences) or more repeats of the selected AON sequences using, for example, PCR-mediated mutagenesis, as already described (34).

In a particular embodiment, the U7-modified AON comprises the sequence shown in SEQ ID NO:2: CATT-CAACTGTTGCCTCCGGTTCTGAAGGTGTTCTTGTAC (SEQ ID NO:2), effect exon 53 skipping in dystrophin pre-mRNA. More particularly, the U7-modified AON effecting exon 53 skipping in dystrophin pre-mRNA is as disclosed in WO2017098187.

In a particular embodiment, the small nuclear RNA-modified AONs, in particular the U7-modified AONs, are vectorized in an AAV vector.

Typically, the viral vector, notably the functional dystrophin-coding vector or the AON-coding vector may also comprise regulatory sequences allowing expression of the encoded functional dystrophin or AONs, such as e.g., a promoter, enhancer internal ribosome entry sites (IRES), sequences encoding protein transduction domains (PTD), and the like. In this regard, the vector most preferably comprises a promoter region, operably linked to the coding sequence, to cause or improve expression of the AON. Such a promoter may be ubiquitous, tissue-specific, strong, weak, regulated, chimeric, etc., to allow efficient and suitable production of the AON. The promoter may be a cellular, viral, fungal, plant or synthetic promoter. Most preferred promoters for use in the present invention shall be functional in muscle cells. Non-limiting examples of muscle-specific promoters include the desmin promoter, the C5-12 synthetic promoter and the muscle creatine kinase (MCK) promoter. For its aspect relating to the expression of an AON, promoters may be selected from small nuclear RNA promoters such as U1, U2, U6, U7 or other small nuclear RNA promoters, or chimeric small nuclear RNA promoters. Other representative promoters include RNA polymerase III-dependent promoters, such as the H1 promoter, or RNA polymerase II-dependent promoters. Examples of regulated promoters include, without limitation, Tet on/off element-containing promoters, rapamycin-inducible promoters and metallothionein promoters. Examples of ubiquitous promoters include viral promoters, particularly the CMV promoter, the RSV promoter, the SV40 promoter, hybrid CBA (Chicken beta actin/CMV) promoter, etc. and cellular promoters such as the PGK (phosphoglycerate kinase) or EF1alpha (Elongation Factor 1alpha) promoters.

The practitioner can use compositions comprising the isolated AON or the viral vector, as described above, in a pharmaceutically acceptable carrier. In addition to the AON or to the virus, a pharmaceutical composition of the present invention may also include a pharmaceutically or physiologically acceptable carrier such as saline, sodium phosphate, etc. The composition will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxy-benzoates, mineral oil, etc. The formulation can also include lubricating agents, wetting agents, emulsifying agents, preservatives, buffering agents, etc. In particular, the present invention involves the administration of an isolated AON or AON-coding virus and is thus somewhat akin to gene therapy. Those of skill in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered via enteral or parenteral routes, e.g. intravenously (i.v.), intra-arterially, subcutaneously, intramuscularly (i.m.), intracerebrally, intracerebroventricularly (i.c.v.), intrathecally (i.t.), intraperitoneally (i.p.), although other types of administration are not precluded.

Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol. While delivery may be either local (i.e. in situ, directly into tissue such as muscle tissue) or systemic, usually delivery will be local to affected muscle tissue, e.g. to skeletal muscle, smooth muscle, heart muscle, etc. Depending on the form of the AON or the viral vector that is administered and the tissue or cell type that is targeted, techniques such as electroporation, sonoporation, a "gene gun" (delivering nucleic acid-coated gold particles), etc. may be employed.

One skilled in the art will recognize that the amount of an isolated AON or of a viral vector to be administered will be an amount that is sufficient to induce amelioration of unwanted muscular dystrophy symptoms. Such an amount may vary inter alia depending on such factors as the gender, age, weight, overall physical condition of the patient, etc. and may be determined on a case by case basis. The amount may also vary according to other components of a treatment protocol (e.g. administration of other medicaments, etc.). Generally, a suitable dose is in the range of from about 1 mg/kg to about 100 mg/kg, and more usually from about 2 mg/kg/day to about 10 mg/kg. In the case of viral-based delivery of AON, suitable doses will depend on different factors such as the virus that is employed, the route of delivery (intramuscular, intravenous, intra-arterial or other), but may typically range from 10e9 to 10e15 viral particles/kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient may be a single event, or the patient is administered with the AON and/or the viral vector on multiple occasions, that may be, depending on the results obtained, several days apart, several weeks apart, or several months apart, or even several years apart.

Combination Therapy with a GDF5 Pathway-Activating Substance

As mentioned above, the present invention relates to a GDF5 pathway-activating substance, for use in a method for the treatment of a muscular disease by gene therapy, in combination with another active ingredient.

Therefore, the invention defines a combination product, comprising a GDF5 pathway-activating substance and another active ingredient suitable for the treatment of a muscular disease.

In a particular embodiment, the combination product comprises a vector, such as a viral vector, in particular an AAV vector, encoding GDF5, such as one of the GDF5 proteins disclosed above.

In yet another embodiment, the combination product comprises recombinant GDF5, in particular recombinant human GDF5, such as one of the GDF5 proteins disclosed above.

In another embodiment, the combination product comprises an active ingredient suitable for the treatment of a muscular diseases, such as:

an AON suitable for exon-skipping within the SOD1 pre-mRNA, for the treatment of ALS;

a vector, such as a viral vector, in particular an AAV vector, comprising a gene encoding a SMN protein, such as the SMN1 or SMN2 gene, more particularly the SMN1 gene;

a vector, such as a viral vector, in particular an AAV vector, comprising a gene encoding a functional dystrophin as described above, for the treatment of DMD; or (i) an AON suitable for exon-skipping within the dystrophin pre-mRNA, or a vector encoding the same, as described above, and (ii) a vector, such as a viral vector, in particular an AAV vector, comprising a gene encoding a functional dystrophin as described above, for the treatment of DMD.

In a further particular embodiment, the components of the combination product are for sequential, separate or simultaneous use. For example, the GDF5 pathway-activating substance may be administered before, during, or after the administration of a gene therapy vector or of an AON.

For example, the GDF5 pathway-activating substance may be administered before administration of an AON, such as an AON for use in the treatment of ALS or DMD.

For example, the GDF5 pathway-activating substance may be administered during administration of an AON, such as an AON for use in the treatment of ALS or DMD. In this embodiment, the GDF5 pathway-activating substance and the AON may be either in the same composition, or in different compositions.

In another example, the GDF5 pathway-activating substance may be administered after administration of an AON, such as an AON for use in the treatment of ALS or DMD.

According to another embodiment, the GDF5 pathway-activating substance may be administered before administration of a gene therapy vector for use in the treatment of a muscular disease, such as a gene therapy vector for the treatment of SMA or DMD as described above.

In a particular embodiment, the GDF5 pathway-activating substance may be administered during administration of a gene therapy vector, such as a gene therapy vector for use in the treatment of a muscular disease, such as a gene therapy vector for the treatment of SMA or DMD as described above.

In this embodiment, the GDF5 pathway-activating substance and the gene therapy vector may be either in the same composition, or in different compositions.

In another particular embodiment, the GDF5 pathway-activating substance may be administered after administration of a gene therapy vector for use in the treatment of a muscular disease, such as a gene therapy vector for the treatment of SMA or DMD as described above.

Below are provided details for the treatment of DMD according to the method in two steps disclosed above. However, one skilled in the art will readily adapt the treatment strategy to other active ingredients and diseases thanks to the information provided herein and the common general knowledge in the field of gene therapy.

The treatment of Duchenne muscular dystrophy, may comprise a two-step administration of:

first an isolated antisense oligonucleotide which is complementary to a part of the dystrophin pre-mRNA and is able to induce exon-skipping during processing of this pre-mRNA to a mRNA; and secondly, a viral vector encoding a Duchenne muscular dystrophy therapeutic product, such as either (i) coding an antisense oligonucleotide able to induce exon-skipping within a dystrophin pre-mRNA, (ii) encoding dystrophin gene-editing means, or (iii) coding a functional dystrophin.

In a particular embodiment, the GDF5 pathway-activating substance may be administered before the first step.

In a further particular embodiment, the GDF5 pathway-activating substance may be administered during the first step.

In another embodiment, the GDF5 pathway-activating substance may be administered between the first step and the second step.

In another embodiment, the GDF5 pathway-activating substance may be administered after the second step.

In a further particular embodiment, the GDF5 pathway-activating substance may be during the second step.

In a particular embodiment, the therapeutic product is an U7-modified AON, in particular an U7-modified AON comprising the sequence shown in SEQ ID NO:2, targeting exon 53 of the dystrophin gene.

As described above, it is believed that the first administration of the isolated AON induces sufficient functional dystrophin expression in muscle cells to secure membrane integrity and therefore limits loss of viral vectors, in particular AON-coding viruses (e.g. AAVs), dystrophin-correcting viruses (e.g. AAVs), or functional dystrophin-coding viruses (e.g. AAVs), due to otherwise repeated cycles of necrosis-regeneration of the dystrophic myofibers.

The time period between the injection of the isolated AON and the viral vector may vary depending on a number of factors, such as the stage of the disease, the age or condition of the patient, and the dosage of the therapy. In any event, the time between the first and second steps of the present method is sufficient for providing a long-lasting benefit of the viral vector treatment. The present method allows the maintenance of high viral therapeutic genome content and improved transgene expression in dystrophic muscles. The consequences of these initial events are a therapeutic benefit stronger of the AAV based therapy lasting longer than the non-combined therapy. Accordingly, the time between the first and second step of the method of the invention may be of from 1 to 40 days, such as at least one or more days, such of 1, 2, 3, 4, 5, 6, 7, 8, 9, 10, 11, 12, 13, 14, 15, 16, 17, 18, 19, 20, 21,22, 23, 24, 25, 26, 27, 28, 29, 30, 31, 32, 33, 34, 35, 36, 37, 38, 39 or 40 days; or of at least one or more weeks, such as at least 1, 2, 3, 4 or 5 weeks. In a particular embodiment, the time period between both administrations is of two weeks (i.e. of about 12 to 16 days, such as of about 12, 13, 14, 15 or 16 days), about three weeks (i.e. of about 19 to 23 days, such as of about 19, 20, 21, 22 or 23 days) or about four weeks (i.e. of about 26-30 days, such as of about 26, 27, 28, 29 or 30 days). More particularly, this time period is comprised between 14 and 28 days, and is more particularly of 12, 13, 14, 15, 16, 17, 18, 19, 20, 21, 22, 23, 24, 25, 26, 27 or 28 days. In another embodiment, the time period between both administrations is of about 14 (i.e 13, 14 or 15 days, more specifically 14 days), 21 (i.e 20, 21 or 22 days, more specifically 21 days) or 28 days (i.e 27, 28 or 29 days, more specifically 28 days).

Further aspects and advantages of the present inventions will be disclosed in the following experimental section, which shall be considered as illustrative only, and not limiting the scope of this application.

LEGEND OF THE FIGURES

FIG. 1. Viral Genomes are Efficiently Maintained in Pip6a-PMO Rescued Mdx Muscles (a) TAs from mdx and wt mice were injected with 1 nmole of Pip6a-PMO two weeks (−2 w) before the injection of 1E+11 vg of the non-therapeutic AAV1-U7scr vector (day 0, d0). Control mdx and wt TAs were injected with AAV1-U7scr vector alone. Four TAs were injected per group. The mice were sacrificed 3 weeks later (3 w). (b) Dystrophin rescue monitored by immunostaining with the NCL-DYS2 monoclonal antibody on transverse sections of TA muscles. One representative immuno-stained section is shown per condition. (c) Dystrophin restoration evaluated by western blotting with NCL-DYS1 monoclonal antibodies (upper panel) on whole protein extracts from the PPMO-treated muscles (lower panel: α-actinin) Dystrophin restoration was quantified by ImageJ software and expressed as the percentage of dystrophin expression in wt muscle. (d) Quantification of AAV genomes by absolute Taqman qPCR. AAV genome content is expressed as the AAV genome number relative to the value obtained for the non PPMO-treated mdx muscles. The data represent the mean values of 4 muscles per group±SEM. n. s.: non-significant, ***$p < 0.001$, Student's t-test. One of two representative experiments is shown.

Figure 2:
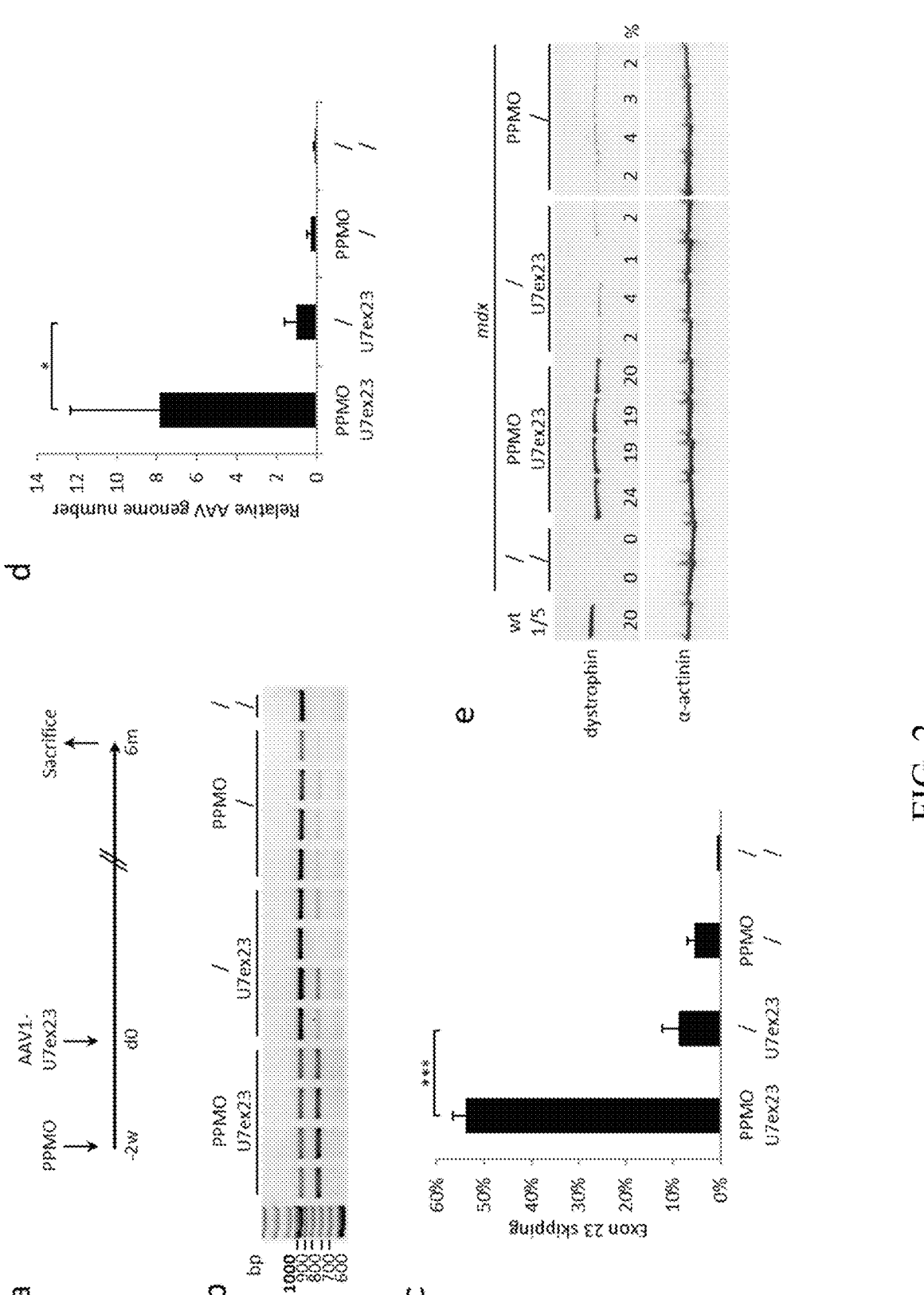

FIG. 2. Pip6a-PMO Pre-Treatment Allows Important Dystrophin Rescue at Low AAV-U7ex23 Dose after 6 Months (a) Mdx TAs were injected with 1 nmole of Pip6a-PMO two weeks (−2w) before the injection of 1E+10 vg of therapeutic AAV1-U7ex23 vector (day 0, d0). Control mdx TAs were injected with PPMO or AAV1-U7ex23 vector alone. Four TAs were injected per group. The mice were sacrificed 6 months later (6m). (b) Level of exon 23 skipping estimated by nested RT-PCR. The 901 bp PCR product corresponds to full-length dystrophin transcripts whereas the 688 bp product corresponds to transcripts lacking exon 23. (c) Quantification of exon 23 skipping performed by relative TaqMan qPCR and expressed as a percentage of total dystrophin transcripts. (d) Quantification of AAV genomes by absolute Taqman qPCR. AAV genome content is expressed as the AAV genome number relative to the value obtained for the non PPMO-treated mdx muscles. The data presented in (c) and (d) represent the mean values of the four TAs per group±SEM. *$p < 0.05$, ***$p < 0.001$, Student's t-test. (e) Dystrophin restoration evaluated by western blotting with NCL-DYS1 monoclonal antibodies (upper panel) on whole protein extracts from the treated muscles (lower panel: α-actinin) Dystrophin restoration was quantified by ImageJ software and expressed as the percentage of dystrophin expression in wt muscle.

Figure 3:
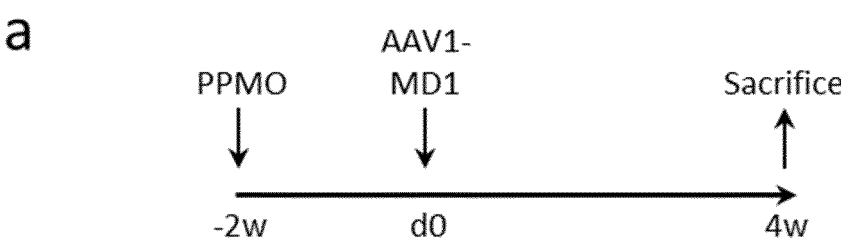
Figure 3:
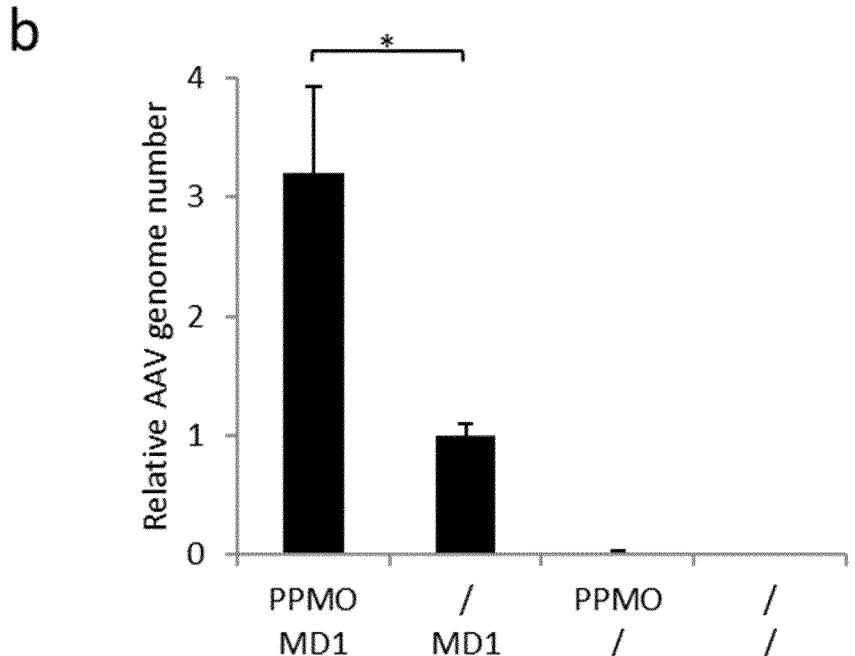
Figure 3:
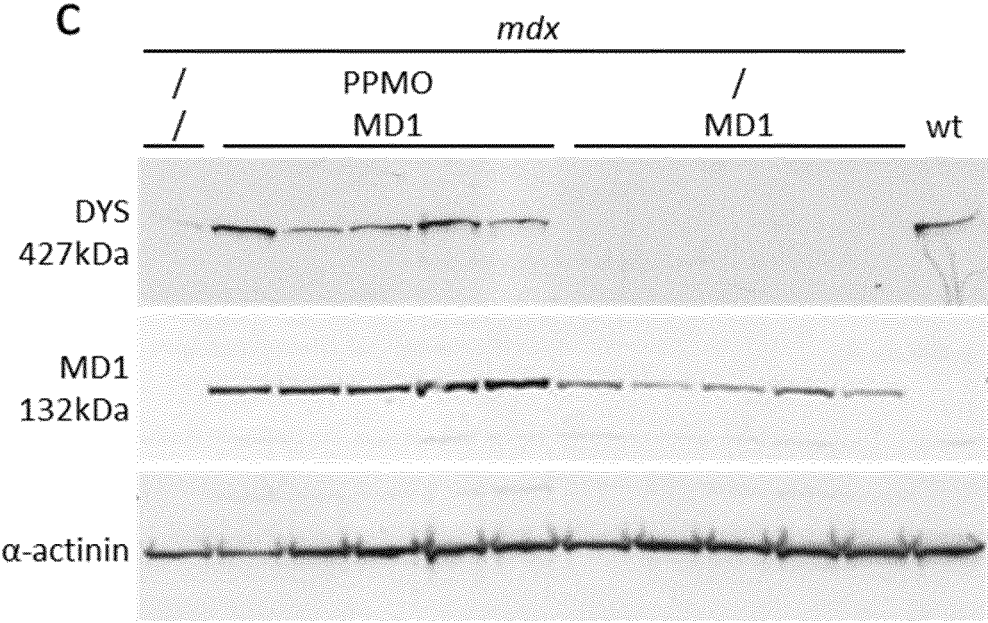

FIG. 3. Effect of Pip6a-PMO Pre-Treatment on AAV1 Mediated Micro-Dystrophin Gene Therapy (a) Mdx TAs were injected with 1 nmole of Pip6a-PMO two weeks (−2w) before injection of 1E+10 vg of AAV1-MD1 micro-dystrophin expressing vector (day 0, d0). Control mdx TAs were injected with PPMO or AAV1-MD1 vector alone. Five TAs were injected per group. The mice were sacrificed 4 weeks later (4 w). (b) Quantification of AAV genomes by absolute Taqman qPCR. AAV genome content is expressed as the AAV genome number relative to the value obtained for the non PPMO-treated mdx muscles. The data represent the mean values of the 5 muscles per group±SEM. *p<0.05, Student's t-test. (c) Expression of PPMO-induced dystrophin (DYS, 427 kDa) and micro-dystrophin (µDYS, 132 kDa) evaluated by western blotting with MANEX1011B monoclonal antibodies (upper panel) on whole protein extracts from the treated muscles (lower panel: α-actinin)

Figure 4:
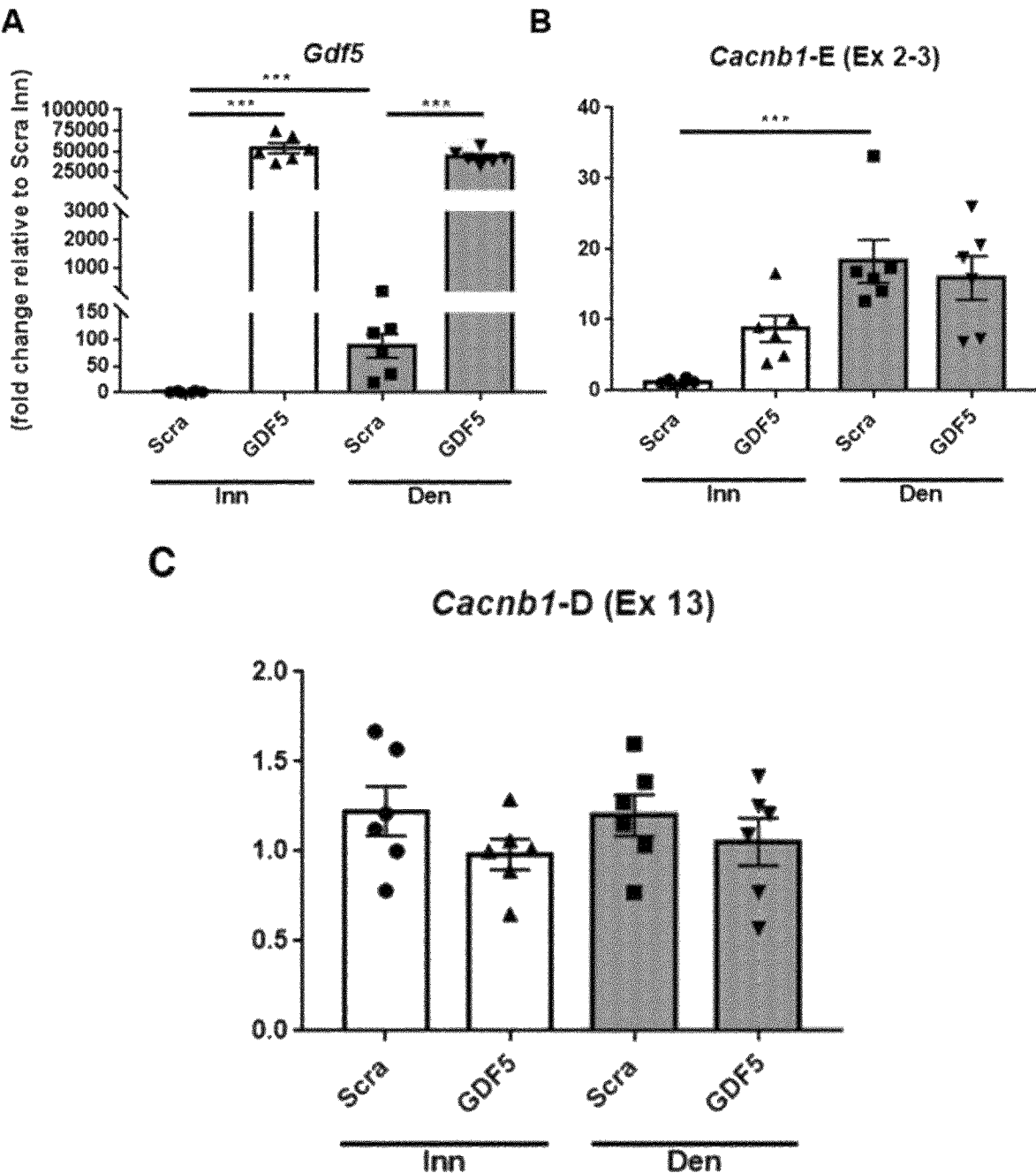
Figure 4:
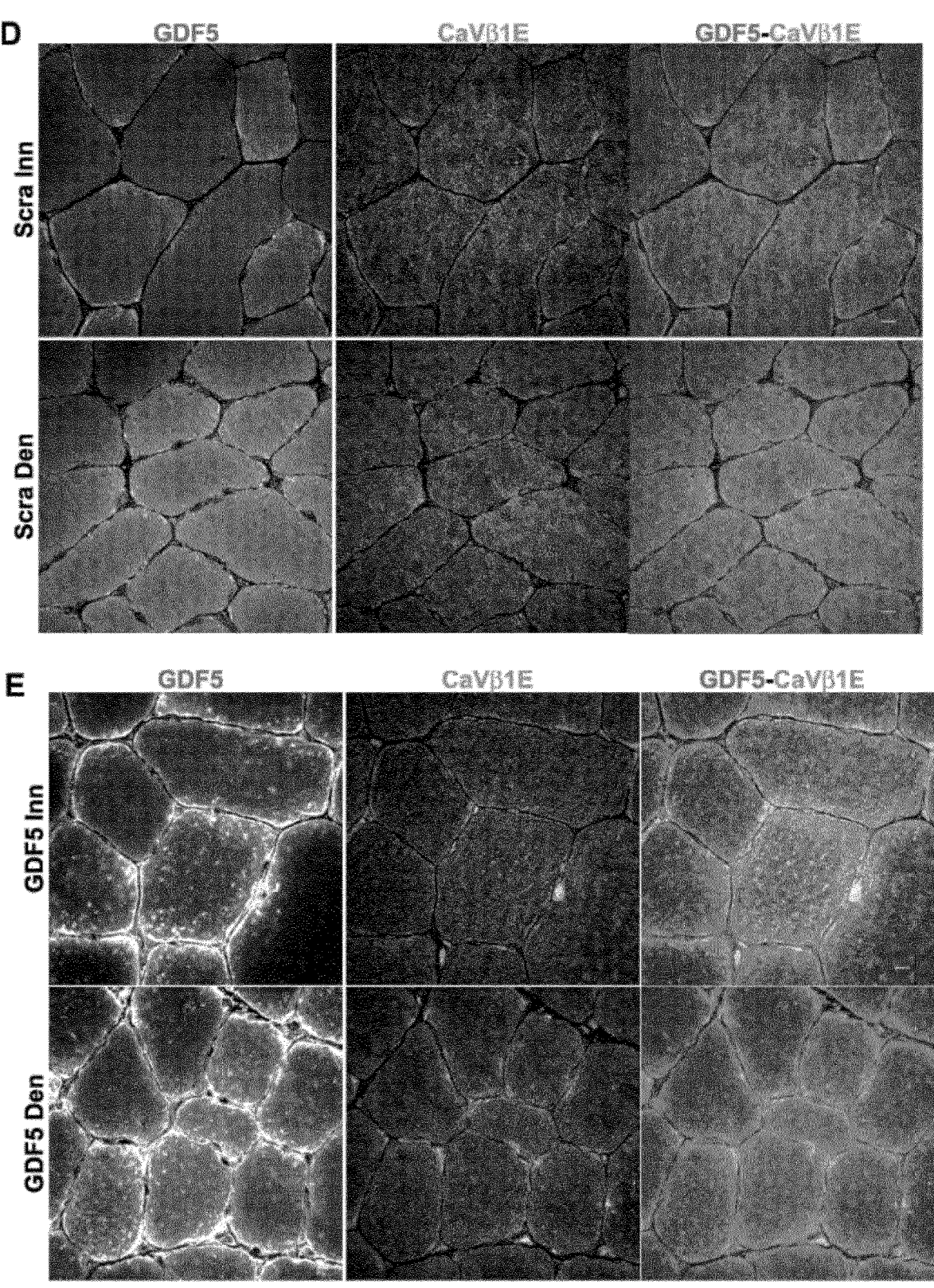
Figure 4:
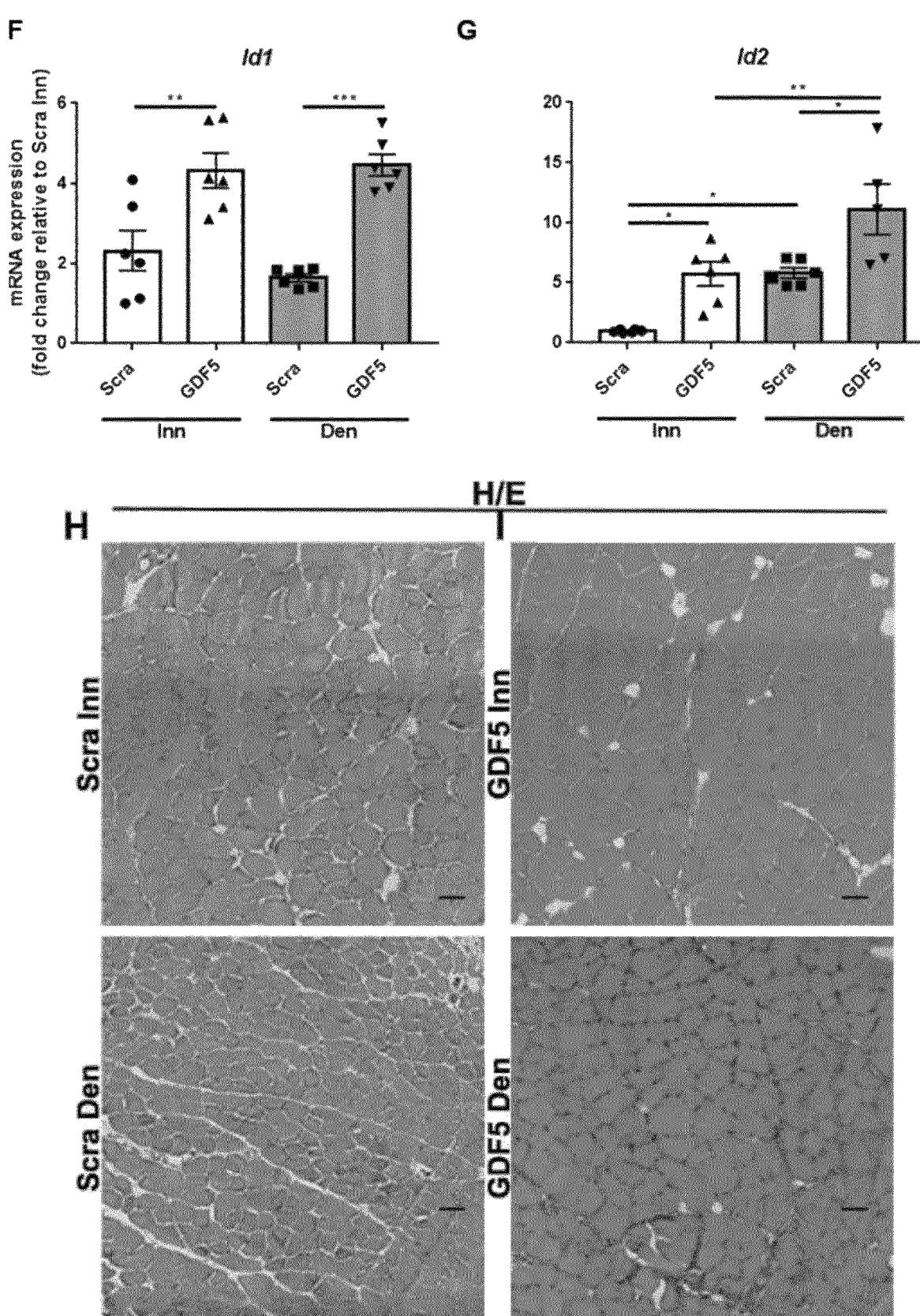
Figure 4:
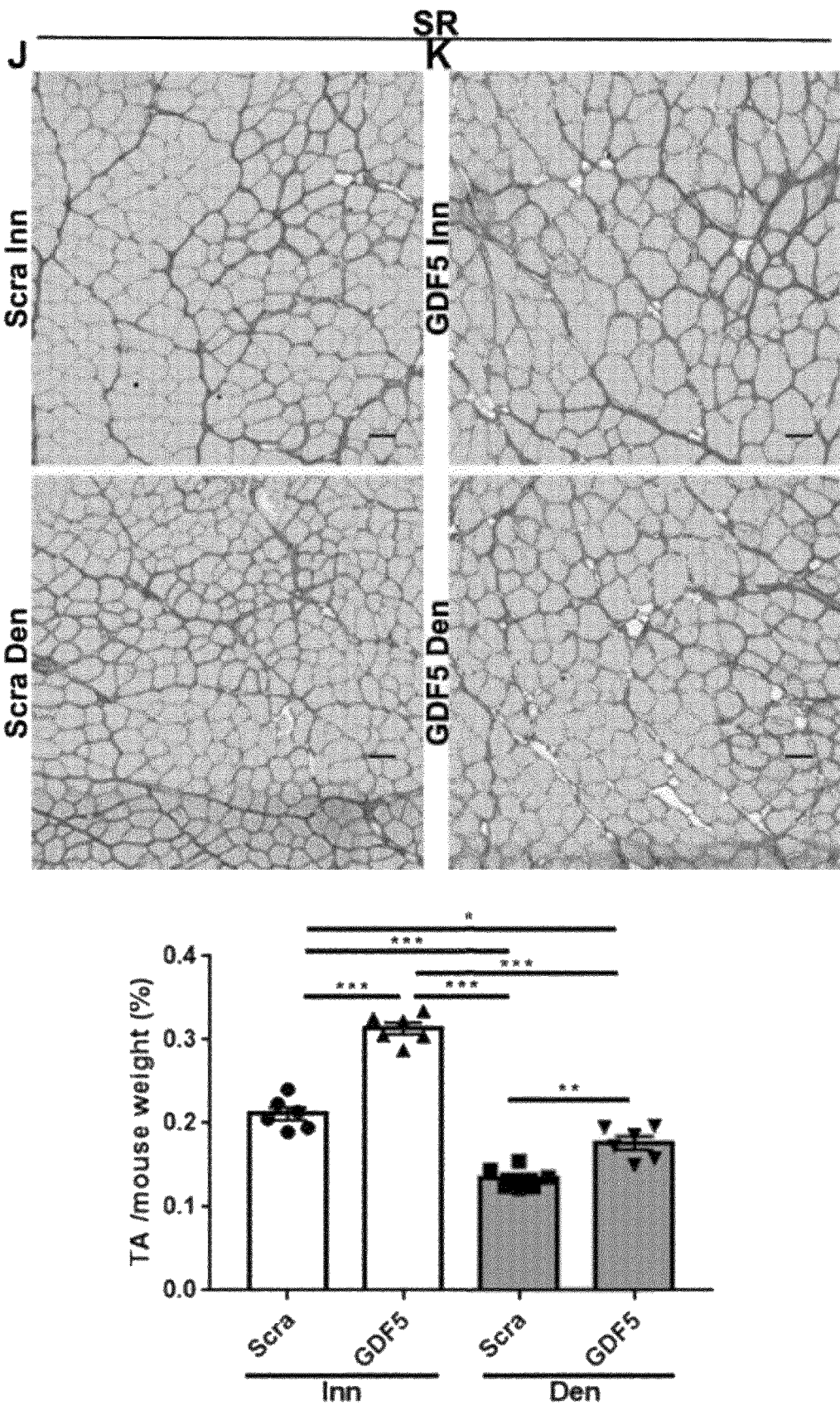

FIG. 4. GDF5 Overexpression in Young Mice Muscle.

A-C: RT-qPCR for (A) Gdf5, (B) Cacnbl-E (Ex2-3) and (C) Cacnbl-D in adult TAs innervated (Inn) or denervated for 15 days (Den) treated with Scra or GDF5. A: minimum medium axis=150; minimum top axis=3000.

D, E: Immunofluorescence images of TA Inn (top) or Den (bottom) treated with (D) Scra or (E) GDF5, stained with GDF5 (Magenta), CaVβ1E (Yellow). Bar: 10 am.

F, G: RT-qPCR for (F) Id1 and (G) Id2 in TAs Inn or Den treated with Scra or GDF5.

H, I: Haematoxylin and eosin (H/E) staining of TAs Inn (top) or Den (bottom) treated with (H) Scra or (I) GDF5. Bar 100 µm.

J, K: Sirius red (SR) staining of TAs Inn (top) or Den (bottom) treated with (J) Scra or (K) GDF5. Bar 100 µm.

L: Muscle/body-weight ratio of Inn or Den adult TAs treated with Scra or GDF5.

A: Means±s.e.m. (n=6) *P<0.05, ***P<0.001, *P<0.05,  P<0.01, *P<0.001; (two stage linear step-up procedure of Benjamini, Krieger and Yekutieli, with Q=1%. Each row was analyzed individually, without assuming a consistent SD).

B, C, F-G, L: Means±s.e.m. (n=6) *P<0.05, ***P<0.001, *P<0.05,  P<0.01, *P<0.001, (ordinary one-way Anova—by Sidak's test).

EXAMPLES

Materials and Methods

Viral Vector Production and Animal Experiments

A three-plasmid transfection protocol was used with pAAV(U7smOPT-SD23/BP22), pAAV(U7smOPT-scr) and codon optimized pΔAR4-R23/ΔCT (MD1) plasmids for generation of single-strand AAV1-U7ex23 (7), AAV1-U7scr (13) and AAV1-MD1 (37) vectors. AAV-GDF5 has been generated by direct cloning of Gdf5 ORF (NM_008109.2), flanked by EcoRI and NheI sites (GeneArt string; ThermoFisher), in pSMD2 AAV2 vectors backbones, under CMV promoter. pSUPER retro puro Scr ShRNA (SCRA) was a gift from John Gurdon (Addgene plasmid #30520). BamHI site has been inserted by PCR and the H1-SCRA cassette has been cloned in pSMD2-sh through BamHI and SalI sites. The final viral preparations were kept in PBS solution at −80° C. Vector titers were determined by real-time PCR and expressed as vector genomes per ml (vg/ml). Three-month-old mdx mice were injected into the Tibialis anterior (TA) muscles with 1 nmole of Pip6a-PMO oligo-nucleotides (GGCCAAACCTCGGCTTACCTGAAAT-SEQ ID NO:11) (20). Additionally, 50 µl of AAV1-U7scr, AAV1-U7ex23 or AAV1-MD1 containing 1E+10 or 1E+11 vg were injected into C57BL/6 (wt) or mdx TAs. AAV-GDF5 was injected into 8 week-old C57BL/6 TAs at 5E+10. As control, 8-week-old C57/BL6 mice were injected using the same procedure with SCRA AAV vector. Mice were sacrificed 10 or 12 weeks after the injection. These animal experiments were performed at the Myology Research Center, Paris, France, according to the guidelines and protocols approved by the Institutional Review Board. A minimum of four mice were injected per group for each experiments. At sacrifice, muscles were collected, snap-frozen in liquid nitrogen-cooled isopentane and stored at −80° C.

Denervation Experiments

Ten weeks after injection of mice with AAV, the sciatic nerve was neuroectomized (ablation of a 5-mm segment of the sciatic nerve) under general anesthesia (Isofluorane, 3% induction, 2% maintenance) with Buprenorphine (vetergesic 1 mg/Kg, subcutaneous). Mice were sacrificed 1, 3, 7 or 15 days after denervation, and TA were dissected, weighed and thereafter frozen in isopentane precooled in liquid nitrogen and stored at −80 ° C. until histology or molecular analysis.

Viral Genome Quantification

Genomic DNA was extracted from mouse muscles using Puregene Blood kit (Qiagen). Copy number of AAV genomes and genomic DNA were measured on 10Ong of genomic DNA by absolute quantitative real-time PCR on a StepOnePlus™ (Applied Biosystems) using the TaqmanR Universal Master Mix (Applied Biosystems). Primers (forward: CTCCAT-CACTAGGGGTTCCTTG (SEQ ID NO:3) and reverse: GTAGATAAGTAGCATGGC (SEQ ID NO:4)) and probe (TAGTTAATGATTAACCC (SEQ ID NO:5)) were used to specifically amplify the viral genome sequence. As a reference sample, a pAAV plasmid was 10-fold serially diluted (from $10^7$ to $10^1$ copies). All genomic DNA samples were analyzed in duplicates.

RT-PCR Analysis

Total RNA was isolated from mouse muscle with Nucleo-Spin® RNA II (Macherey-Nagel), and reverse transcription (RT) performed on 200ng of RNA by using the Super-script™ II and random primers (Life technologies). Non-skipped and skipped dystrophin transcripts were detected by nested PCR and quantified as described (9).

Gene Expression Analysis by RT-QPCR

Total RNA was prepared from TA cryosections using TRizol (Life Technologies) following the manufacturer's instructions. Complementary DNA was generated with Superscript II Reverse transcriptase (Life Technologies), amplified using PCR Master Mix (M7505, Promega) for RT-PCR oranalyzed by real-time qPCR. Real-time qPCR was performed on StepOne Plus Real-Time PCR System (Applied Biosystems) using Power SyberGreen PCR MasterMix (Applied Biosystems). All data were analyzed using the ΔΔCT method and normalized to PO (mouse acidic ribosomal phosphoprotein) mRNA expression levels. The sample reference to calculate mRNA fold change is indicated in each panel. Primers used are listed

| Gene Name | Primer Sequence | Specie |
|---|---|---|
| PO fw | CTCCAAGCAGATGCAGCAGA | mouse |
| PO rv | ATAGCCTTGCGCATCATGGT | mouse |
| Id-2 fw | CTCCAAGCTCAAGGAACTGG | mouse |
| Id-2 rv | ATTCAGATGCCTGCAAGGAC | mouse |
| Id-1 fw | AGTGAGCAAGGTGGAGATCC | mouse |
| Id-1 rv | GATCGTCGGCTGGAACAC | mouse |

-continued

| Gene Name | Primer Sequence | Specie |
|-----------|-----------------|--------|
| Gdf5 fw | ATGCTGACAGAAAGGGAGGTAA | mouse |
| Gdf5 rv | GCACTGATGTCAAACACGTACC | mouse |

Western Blot Analysis

Protein extracts were obtained from pooled muscle sections treated with 125 mM sucrose, 5 mM Tris-HCl pH 6.4, 6% of XT Tricine Running Buffer (Bio-Rad), 10% SDS, 10% Glycerol, 5% β-mercaptoethanol. The samples were purified with the Pierce Compat-Able™ Protein Assay preparation Reagent Set (Thermo Scientific) and the total protein concentration was determined with the Pierce BCA Protein Assay Kit (Thermo Scientific). Samples were denatured at 95° C. for 5 minutes and 100 μg of protein were loaded onto Criterion XT Tris-acetate precast gel 3-8% (Bio-Rad). Membrane was probed with primary monoclonal antibodies directed against dystrophin (NCL-DYS1, 1:50, Leica Biosystems; MANEX1011B, 1:50, kindly gifted by The Muscular Dystrophy Association Monoclonal Antibody Resource (38)) and α-actinin (1:1000, Sigma-Aldrich), followed by incubation with a sheep anti-mouse secondary antibody (horseradish peroxidase conjugated; 1:15000) and Pierce ECL Western Blotting Substrate (Thermo Scientific).

Immunohistochemistry and Histology

TA sections of 12 μm were cut and examined for dystrophin expression using the NCL-DYS2 monoclonal antibody (Leica Biosystems). Rabbit polyclonal antibody for 041 C-terminus (AP16144b) was purchased from AbGent and the mouse monoclonal to GDF5 was obtained by Santa Cruz Biotechnologies (SC-373744). Fluorescent secondary antibodies goat anti-rabbit and goat anti-mouse were purchased from Life technologies.

For H&E staining, sections were fixed in 4% PFA for 10 min, washed in PBS and then stained in haematoxylin for 5 min and eosin for 30 sec. The muscle sections were further dried in gradually increasing concentration of ethanol/water solutions and, after fixation in 100% xylene, were mounted in Vectamount (Vector Laboratories). Sirius Red staining was performed to analyze total collagen I and III content. Muscle cryosections were fixed in PFA 4% for 10 min, washed in water and dried in 100% ethanol for 5 min. Sections were then stained in Picro-Sirius Red (0.3%) solution for 1 h while protected from light. After a washing in acidified water (5 min in acetic acid 0.5% vol/vol), sections were fixed in 100% ethanol (3 washes for 5 min) and the final dehydration was performed in xylene 100%, mounted in Vectamount and visualized using a macroscope Nikon AZ100. Confocal images were taken with Leica SPE or a Nikon Ti2 microscope equipped with a motorized stage and a Yokogawa CSU-W1 spinning disk head coupled with a Prime 95 sCMOS camera (Photometrics).

Results

Effect of Dystrophin Restoration by AON Pre-Treatment on Non-Therapeutic Viral Genome Maintenance In order to induce temporary dystrophin expression at the sarcolemma of Mdx myofibers, Mdx Tibialis anterior (TA) muscles were injected with 11 μg of Pip6a-PMO (20), a peptide-phosphorodiamidate morpholino (PPMO) antisense oligonucleotide that is particularly efficient for mdx exon skipping. The non-therapeutic AAV-U7scr vectors (carrying a scrambled, non-specific sequence) were injected in the same muscles two weeks later (FIG. 1a), when dystrophin rescue was optimal, at a high dose (1E+11 viral genomes). We had previously shown that these U7scr vectors, which are unable to induce exon skipping and thereby to rescue dystrophin expression, are drastically lost within three weeks from dystrophin-deficient mdx muscle (13).

Following AON pre-treatment inducing exon skipping, three weeks after AAV1-U7scr injection, immunofluorescence staining revealed a strong dystrophin restoration and its correct localization at the sarcolemma in mdx injected muscles (FIG. 1b). Dystrophin levels were quantified in mdx muscles by western blotting and showed that the AON pre-treatment resulted in 56 to 98% of quasi-dystrophin restoration compared to normal levels (FIG. 1c). As expected (13), the viral genome content analyzed by quantitative PCR (qPCR) was 6 times higher in wild-type muscles (wt) than in non AON treated mdx muscles. Interestingly, the viral genome content analyzed by qPCR in the mdx AON treated group is similar to the one observed in wt muscles (FIG. 1d). Therefore, a significant dystrophin expression induced by PPMO pre-treatment at the time of AAV1-U7scr injection protects against the rapid loss of AAV1-U7scr genomes in mdx muscles comparable to what was observed in wt muscles.

Effect of Pip6a-PMO Pre-Treatment on Dystrophin Rescue at Low Dose of Therapeutic AAV-U7ex23

AAV1 vectors encoding the U7ex23 (AAV1-U7ex23) allow efficient exon 23 skipping and therefore quasi-dystrophin rescue in the mdx muscles. To evaluate the benefit of an AON pre-treatment on the quasi-dystrophin rescue via AAV1-U7ex23, we injected 11 μg of Pip6a-PMO antisense oligonucleotides into mdx TAs two weeks before injection of AAV1-U7ex23 vectors (FIG. 2A). A low vector dose (1E+10 viral genomes) was chosen as this dose allows a weak quasi-dystrophin rescue (less than 5% of the normal levels) (13).

The benefit of AAV1-U7ex23 injection was analysed six months later when dystrophin rescue induced by the single PPMO injection was nearly abolished. Levels of exon 23 skipping analyzed by nested RT-PCR (FIG. 2b) and quantified by qPCR (FIG. 2c) in mdx TAs treated with AAV1-U7ex23 or PPMO alone were low as expected, respectively 9 and 6% of skipped transcripts, leading to the synthesis of rescued dystrophin around 2% of the normal level (FIG. 2e). Conversely, TAs treated sequentially with PPMOs and AAV1-U7ex23 showed 54% of skipped transcripts (FIGS. 2c) and 20% of the normal levels of dystrophin (FIG. 2e). AAV genome copy number quantified by absolute qPCR was 8 fold higher in the dual PPMO/AAV1-U7ex23 treated muscles than in AAV1-U7ex23 only injected muscles (FIG. 2D). These data demonstrate that the PPMO pre-treatment allowed a better maintenance of the therapeutic U7ex23 genomes in the mdx muscles six months after the AAV-U7 injections and remarkably resulted in a 10 fold improvement of the rescued dystrophin amount.

Pip6a-PMO Pre-Treatment Significantly Increases the Efficacy of AAV1 Mediated Micro-Dystrophin Gene Therapy To evaluate the efficacy of an AON pre-treatment on AAV-micro-dystrophin gene therapy, we injected Pip6a-PMO AONs into mdx TAs two weeks before injection of AAV1-MD1 vector (1E+10 vg) expressing a murine micro-dystrophin (MD1) (37) (FIG. 3a). Four weeks later, a strong dystrophin restoration was observed in PPMO-treated mdx TAs induced by the PPMO pre-treatment (FIG. 3c). AAV genome copy number and micro-dystrophin expression were 3-fold higher in the PPMO/AAV1-MD1 treated muscles than in AAV1-MD1 only treated muscles (FIG. 3b & c), illustrating the PPMO pre-treatment benefit on AAV-microdystrophin gene therapy. This experiment establishes the proof of concept that the AON pre-treatment is capable of enhancing all AAV-based gene therapies for DMD.

Effect of GDF5 Overexpression

We overexpressed GDF5 in young TAs (FIG. 4A, D, E) which induced Cacnb1-E transcription in innervated TAs compared to scrambled (FIG. 4 B, D, E) without affecting Cacnb1-D expression (FIG. 4 C). Nevertheless, GDF5 overexpression and its activated signaling checked by Id-1 and Id-2 transcription (FIG. 4 F, G) increased mostly innervated muscle mass (FIG. 4 H-L).

Discussion

AAV genomes are rapidly lost from dystrophic muscles during AAV-U7-mediated exon-skipping therapy, certainly because of their episomal nature and the fragility of the dystrophic muscle fibers that undergo cycles of necrosis/generation, show abnormally leaky membranes, and in addition are characterized by increased excretion of exosomes and microparticles (36). We showed here that a significant (>60%) quasi-dystrophin rescue following PPMO pre-treatment at the moment of AAV-U7 injections allows an efficient maintenance of the viral genomes in mdx muscles three weeks later. Additionally, this initial maintenance of viral genomes increases quasi-dystrophin restoration by AAV-U7, around 6 fold at RNA level and around 10 fold at protein level six months later.

The PPMO pre-treatment resulted in substantial dystrophin expression at the time of AAV-U7 injection. This likely reduces, like in normal control muscle, the membrane abnormalities leading to AAV genome loss before AAV-U7 induced quasi-dystrophin expression occurs. Once established, a AAV-U7 mediated high quasi-dystrophin expression will be maintained because it will by itself prevent transgene loss. Hence, by allowing the maintenance of high viral genome content in the critical period between AAV injection and AAV-mediated transgene expression in the treated dystrophic muscles, PPMO-mediated quasi-dystrophin restoration guarantees a long-lasting benefit of AAV-U7 treatment.

This pre-treatment could be induced by any AONs allowing substantial quasi-dystrophin rescue (i.e. using different skippable mutations and different target sequences and different AON chemistries such as tricyclo-DNA (36)) using the principle demonstrated here with the PPMO chemistry.

This AON pre-treatment is applicable to all therapeutic approaches for Duchenne myopathy using AAV vectors, in particular AAV-U7-mediated exon skipping and classical gene therapy with transfer of functional micro-dystrophin cDNAs into muscles, as demonstrated thanks to the data presented herein.

In addition, it is herein shown that muscle mass is increased when GDF5 is overexpressed, meaning that muscles to be treated can further be protected during the application of the above therapeutic strategy thanks to the administration of either a vector expressing GDF5, or a recombinant GDF5 protein.

On the eve of clinical trials using AAV-based therapies for DMD patients, this study underscores the strong impact of combined approaches to improve the benefit of AAV-based therapies allowing the use of lower and thus safer vector doses for a larger level of dystrophin expression in the long term.

REFERENCES

1. Harper, S. Q., Hauser, M. A., DelloRusso, C., Duan, D., Crawford, R. W., Phelps, S. F., Harper, H. A., Robinson, A. S., Engelhardt, J. F., Brooks, S. V. et al. (2002) Modular flexibility of dystrophin: implications for gene therapy of Duchenne muscular dystrophy. Nat. Med., 8, 253-261.
2. Goemans, N. M., Tulinius, M., van den Akker, J. T., Burm, B. E., Ekhart, P. F., Heuvelmans, N., Holling, T., Janson, A. A., Platenburg, G. J., Sipkens, J. A. et al. (2011) Systemic administration of PRO051 in Duchenne's muscular dystrophy. N. Engl. J. Med., 364, 1513-1522.
3. Cirak, S., Arechavala-Gomeza, V., Guglieri, M., Feng, L., Torelli, S., Anthony, K., Abbs, S., Garralda, M. E., Bourke, J., Wells, D. J. et al. (2011) Exon skipping and dystrophin restoration in patients with Duchenne muscular dystrophy after systemic phosphorodiamidate morpholino oligomer treatment: an open-label, phase 2, dose-escalation study. Lancet, 378, 595-605.
4. Mendell, J. R., Rodino-Klapac, L. R., Sahenk, Z., Roush, K., Bird, L., Lowes, L. P., Alfano, L., Gomez, A. M., Lewis, S., Kota, J. et al. (2013) Eteplirsen for the treatment of Duchenne muscular dystrophy. Ann. Neurol., 74, 637-647.
5. Voit, T., Topaloglu, H., Straub, V., Muntoni, F., Deconinck, N., Campion, G., de Kimpe, S. J., Eagle, M., Guglieri, M., Hood, S. et al. (2014) Safety and efficacy of drisapersen for the treatment of Duchenne muscular dystrophy (DEMAND II): an exploratory, randomised, placebo-controlled phase 2 study. Lancet Neurol., 13, 987-996.
6. Brun, C., Suter, D., Pauli, C., Dunant, P., Lochmuller, H., Burgunder, J. M., Schumperli, D. and Weis, J. (2003) U7 snRNAs induce correction of mutated dystrophin pre-mRNA by exon skipping. Cell Mol. Life Sci., 60, 557-566.
7. Goyenvalle, A., Vulin, A., Fougerousse, F., Leturcq, F., Kaplan, J. C., Garcia, L. and Danos, O. (2004) Rescue of dystrophic muscle through U7 snRNA-mediated exon skipping. Science, 306, 1796-1799.
8. Denti, M. A., Rosa, A., D'Antona, G., Sthandier, O., De Angelis, F. G., Nicoletti, C., Allocca, M., Pansarasa, O., Parente, V., Musaro, A. et al. (2006) Chimeric adeno-associated virus/antisense U1 small nuclear RNA effectively rescues dystrophin synthesis and muscle function by local treatment of mdx mice. Hum. Gene Ther., 17, 565-574.
9. Goyenvalle, A., Babbs, A., Wright, J., Wilkins, V., Powell, D., Garcia, L. and Davies, K. E. (2012) Rescue of severely affected dystrophin/utrophin-deficient mice through scAAV-U7snRNA-mediated exon skipping. Hum. Mol. Genet., 21, 2559-2571.
10. Bish, L. T., Sleeper, M. M., Forbes, S. C., Wang, B., Reynolds, C., Singletary, G. E., Trafny, D., Morine, K. J., Sanmiguel, J., Cecchini, S. et al. (2012) Long-term restoration of cardiac dystrophin expression in golden retriever muscular dystrophy following rAAV6-mediated exon skipping. Mol. Ther., 20, 580-589.
11. Vulin, A., Barthelemy, I., Goyenvalle, A., Thibaud, J. L., Beley, C., Griffith, G., Benchaouir, R., Le, H. M., Unterfinger, Y., Lorain, S. et al. (2012) Muscle function recovery in golden retriever muscular dystrophy after AAV1-U7 exon skipping. Mol. Ther., 20, 2120-2133.
12. Lorain, S., Gross, D. A., Goyenvalle, A., Danos, O., Davoust, J. and Garcia, L. (2008) Transient immunomodulation allows repeated injections of AAV1 and correction of muscular dystrophy in multiple muscles. Mol. Ther., 16, 541-547.

13. Le Hir, M., Goyenvalle, A., Peccate, C., Precigout, G., Davies, K. E., Voit,T., Garcia, L. and Lorain, S. (2013) AAV Genome Loss From Dystrophic Mouse Muscles During AAV-U7 snRNA-mediated Exon-skipping Therapy. Mol. Ther., 21, 1551-1558.

14. Cartegni, L., Chew, S. L., and Krainer, A. R. (2002). Listening to silence and understanding nonsense: exonic mutations that affect splicing. Nat Rev Genet 3, 285-298.

15. Reed, R., and Maniatis, T. (1988). The role of the mammalian branchpoint sequence in pre-mRNA splicing. Genes & development 2, 1268-1276.

16. Aartsma-Rus, A., van Vliet, L., Hirschi, M., Janson, A. A., Heemskerk, H., de Winter, C. L., de Kimpe, S., van Deutekom, J. C., t Hoen, P. A., and van Ommen, G. J. (2009). Guidelines for antisense oligonucleotide design and insight into splice-modulating mechanisms. Mol Ther 17, 548-553.

17. Brown S C, Fassati A, Popplewell L, Page A M, Henry M D, Campbell K P, Dickson G. Dystrophic phenotype induced in vitro by antibody blockade of muscle alpha-dystroglycan-laminin interaction. J Cell Sci. 1999 January; 112 (Pt 2):209-16.

18. Kumar, P., Wu, H., McBride, J. L., Jung, K. E., Kim, M. H., Davidson, B. L., Lee, S. K., Shankar, P., and Manjunath, N. (2007). Transvascular delivery of small interfering RNA to the central nervous system. Nature 448, 39-43.

19. Betts, C., Saleh, A. F., Arzumanov, A. A., Hammond, S. M., Godfrey, C., Coursindel, T., Gait, M. J., and Wood, M. J. (2012). Pip6-PMO, A New Generation of Peptide-oligonucleotide Conjugates With Improved Cardiac Exon Skipping Activity for DMD Treatment. Molecular therapy Nucleic acids 1, e38.

20. Lehto, T., Castillo, A. A., Gauck, S., Gait, M. J., Coursindel, T., Wood, M. J., Lebleu, B. and Boisguerin, P. (2014) Cellular trafficking determines the exon skipping activity of Pip6a-PMO in mdx skeletal and cardiac muscle cells. Nucleic Acids Res., 42, 3207-3217.

21. Yamada, T., Das Gupta, T. K., and Beattie, C. W. (2013). p28, an anionic cell-penetrating peptide, increases the activity of wild type and mutated p53 without altering its conformation. Molecular pharmaceutics 10, 3375-3383.

22. Malhotra, M., Tomaro-Duchesneau, C., Saha, S., Kahouli, I., and Prakash, S. (2013). Development and characterization of chitosan-PEG-TAT nanoparticles for the intracellular delivery of siRNA. International journal of nanomedicine 8, 2041-2052.

23. Lundberg, M., Wikstrom, S., and Johansson, M. (2003). Cell surface adherence and endocytosis of protein transduction domains. Mol Ther 8, 143-150.

24. Lu, Q. L., Mann, C. J., Lou, F., Bou-Gharios, G., Morris, G. E., Xue, S. A., Fletcher, S., Partridge, T. A. and Wilton, S. D. (2003) Functional amounts of dystrophin produced by skipping the mutated exon in the mdx dystrophic mouse. Nat. Med., 9, 1009-1014.

25. Gregorevic P, Allen J M, Minami E, Blankinship M J, Haraguchi M, Meuse L, Finn E, Adams M E, Froehner S C, Murry C E, Chamberlain J S. rAAV6-microdystrophin preserves muscle function and extends lifespan in severely dystrophic mice. Nat Med. 2006 July; 12(7):787-9.

26. Koo T, Okada T, Athanasopoulos T, Foster H, Takeda S, Dickson G. Long-term functional adeno-associated virus-microdystrophin expression in the dystrophic CXMDj dog. J Gene Med. 2011 September; 13(9):497-506.

27. Shin J H, Pan X, Hakim C H, Yang H T, Yue Y, Zhang K, Terjung R L, Duan D. Microdystrophin ameliorates muscular dystrophy in the canine model of duchenne muscular dystrophy. Mol Ther. 2013 April; 21(4): 750-7

28. Mendell J R, Campbell K, Rodino-Klapac L, Sahenk Z, Shilling C, Lewis S, Bowles D, Gray S, Li C, Galloway G, Malik V, Coley B, Clark K R, Li J, Xiao X, Samulski J, McPhee S W, Samulski R J, Walker C M. Dystrophin immunity in Duchenne's muscular dystrophy. N Engl J Med. 2010 Oct. 7; 363(15):1429-37.

29. Gao, G., Vandenberghe, L. H., Alvira, M. R., Lu, Y., Calcedo, R., Zhou, X., and Wilson, J. M. (2004). Clades of Adeno-associated viruses are widely disseminated in human tissues. J Virol 78, 6381-6388.

30. Gao, G. P., Alvira, M. R., Wang, L., Calcedo, R., Johnston, J., and Wilson, J. M. (2002). Novel adeno-associated viruses from rhesus monkeys as vectors for human gene therapy. Proc Natl Acad Sci USA 99, 11854-11859.

31. McCarty, D. M., Monahan, P E, and Samulski, R. J. (2001). Self-complementary recombinant adeno-associated virus (scAAV) vectors promote efficient transduction independently of DNA synthesis. Gene Ther 8, 1248-1254.

32. Cazzella, V., Martone, J., Pinnaro, C., Santini, T., Twayana, S. S., Sthandier, O., D'Amico, A., Ricotti, V., Bertini, E., Muntoni, F., et al. (2012). Exon 45 skipping through U1-snRNA antisense molecules recovers the Dys-nNOS pathway and muscle differentiation in human DMD myoblasts. Mol Ther 20, 2134-2142.

33. De Angelis, F. G., Sthandier, O., Berarducci, B., Toso, S., Galluzzi, G., Ricci, E., Cossu, G., and Bozzoni, I. (2002). Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci U S A 99, 9456-9461.

34. Goyenvalle, A., Vulin, A., Fougerousse, F., Leturcq, F., Kaplan, J. C., Garcia, L., and Danos, O. (2004). Rescue of dystrophic muscle through U7 snRNA-mediated exon skipping. Science 306, 1796-1799.

35. Schumperli, D., and Pillai, R. S. (2004). The special Sm core structure of the U7 snRNP: far-reaching significance of a small nuclear ribonucleoprotein. Cell Mol Life Sci 61, 2560-2570.

36. Duguez, S., Duddy, W., Johnston, H., Laine, J., Le Bihan, M. C., Brown, K. J., Bigot, A., Hathout, Y., Butler-Browne, G. and Partridge, T. (2013) Dystrophin deficiency leads to disturbance of LAMP1-vesicle-associated protein secretion. Cell Mol. Life Sci., 70, 2159-2174.

37. Foster, H., Sharp, P. S., Athanasopoulos, T., Trollet, C., Graham, I. R., Foster, K., Wells, D. J., Dickson, G. (2008) Codon and mRNA sequence optimization of microdystrophin transgenes improves expression and physiological outcome in dystrophic mdx mice following AAV2/8 gene transfer. Mol. Ther., 16, 1825-1832.

38. Bartlett, R. J., Stockinger, S., Denis, M. M., Bartlett, W. T., Inverardi, L., Le, T. T., thi Man, N., Morris, G. E., Bogan, D. J., Metcalf-Bogan, J., Kornegay, J. N. (2000) In vivo targeted repair of a point mutation in the canine dystrophin gene by a chimeric RNA/DNA oligonucleotide. Nat. Biotechnol., 18, 615-622.

The invention claimed is:

1. A kit comprising:

a GDF5 pathway-activating substance; and at least one other active ingredient, wherein the GDF5 pathway-activating substance is selected from a synthetic or recombinant GDF5 peptide, and a vector comprising a nucleic acid encoding GDF5;

wherein the at least one other active ingredient comprises an isolated antisense oligonucleotide (AON) capable of inducing an exon-skipping in a dystrophin pre-mRNA and a Duchenne muscular dystrophy therapeutic viral vector encoding:

an antisense oligonucleotide able to induce exon-skipping within a dystrophin pre-mRNA;

a dystrophin gene-editing means; or a functional dystrophin protein.

2. The kit according to claim 1, wherein the GDF5 pathway-activating substance is a vector comprising a gene encoding GDF5.

3. The kit according to claim 1, wherein the GDF5 pathway-activating substance is recombinant GDF5.

4. The kit according to claim 2, wherein the GDF5 pathway activating substance is a plasmid or viral vector comprising a gene encoding GDF5.

5. The kit according to claim 4, wherein the GDF5 pathway activating substance is an AAV vector encoding human GDF5.

6. The kit according to claim 3, wherein the GDF5 pathway activating substance is recombinant human GDF5.

*    *    *    *    *